(12) United States Patent
Ochi et al.

(10) Patent No.: US 11,166,629 B2
(45) Date of Patent: Nov. 9, 2021

(54) VIDEO NEEDLE SYRINGE

(71) Applicant: Samark Technology LLC, Sarasota, FL (US)

(72) Inventors: Sam Seiichiro Ochi, Lakewood Ranch, FL (US); Mark Walter, Sarasota, FL (US)

(73) Assignee: NANOSURGERY TECHNOLOGY CORPORATION, Sarasota, FL (US)

( * ) Notice: Subject to any disclaimer, the term of this patent is extended or adjusted under 35 U.S.C. 154(b) by 507 days.

(21) Appl. No.: 15/721,376

(22) Filed: Sep. 29, 2017

(65) Prior Publication Data

US 2018/0084986 A1   Mar. 29, 2018

Related U.S. Application Data

(60) Provisional application No. 62/401,784, filed on Sep. 29, 2016.

(51) Int. Cl.
*A61B 1/07*   (2006.01)
*A61B 17/34*   (2006.01)
(Continued)

(52) U.S. Cl.
CPC ............ *A61B 1/317* (2013.01); *A61B 1/0011* (2013.01); *A61B 1/00078* (2013.01); *A61B 1/00087* (2013.01); *A61B 1/00091* (2013.01); *A61B 1/00114* (2013.01); *A61B 1/015* (2013.01); *A61B 1/051* (2013.01); *A61B 1/0669* (2013.01); *A61B 1/07* (2013.01); *A61B 17/34* (2013.01); *A61B 17/3474* (2013.01);
(Continued)

(58) Field of Classification Search
CPC . A61B 1/317; A61B 1/00078; A61B 1/00087; A61B 1/00091; A61B 1/0011; A61B 1/00114; A61B 1/015; A61B 1/051; A61B 1/0669; A61B 1/07; A61B 17/34; A61B 17/3474; A61B 17/3496; A61M 5/3293; A61M 2205/584

See application file for complete search history.

(56) References Cited

U.S. PATENT DOCUMENTS 4,900,303 A * 2/1990 Lemelson .......... A61B 5/02154
                                                            604/11
5,345,592 A * 9/1994 Woodmas .............. H04B 3/548
                                                            725/130
(Continued)

FOREIGN PATENT DOCUMENTS

JP   2007-503938 A   3/2007

OTHER PUBLICATIONS

International Search Report and Written Opinion for PCT/US2017/054569 dated Jan. 10, 2018.

*Primary Examiner* — John P Leubecker
*Assistant Examiner* — Shankar Raj Ghimire

(57) ABSTRACT

An imaging apparatus includes a hub; a needle extending from the hub, a probe provided within the needle and configured to extend and retract, an imager disposed in the probe, and an interposer provided within the needle. The imager is configured to generate an imaging signal. The interposer includes a substrate and a conductive line patterned on the substrate. The interposer is configured to receive the image signal from the imager via the conductive line.

9 Claims, 30 Drawing Sheets
(28 of 30 Drawing Sheet(s) Filed in Color)

(51) Int. Cl.
*A61B 1/317* (2006.01)
*A61B 1/00* (2006.01)
*A61B 1/015* (2006.01)
*A61B 1/06* (2006.01)
*A61B 1/05* (2006.01)
*A61M 5/32* (2006.01)

(52) U.S. Cl.
CPC ....... *A61B 17/3496* (2013.01); *A61M 5/3293* (2013.01); *A61M 2205/584* (2013.01)

(56) References Cited

U.S. PATENT DOCUMENTS

| | | | | |
|---|---|---|---|---|
| 5,588,432 | A * | 12/1996 | Crowley | A61B 5/02007 600/374 |
| 5,879,289 | A * | 3/1999 | Yarush | A61B 1/00039 600/109 |
| 5,993,378 | A * | 11/1999 | Lemelson | A61B 1/00096 600/109 |
| 6,387,043 | B1 * | 5/2002 | Yoon | A61B 1/00052 600/104 |
| 6,554,765 | B1 * | 4/2003 | Yarush | A61B 1/00039 348/73 |
| 8,834,358 | B2 * | 9/2014 | Mckinley | A61B 17/3421 600/117 |
| 9,622,646 | B2 * | 4/2017 | Ouyang | A61B 1/00103 |
| 10,362,926 | B2 * | 7/2019 | Ouyang | A61B 1/05 |
| 10,463,399 | B2 * | 11/2019 | Savvouras | A61B 1/015 |
| 2004/0176732 | A1 | 9/2004 | Frazier et al. | |
| 2007/0167681 | A1 * | 7/2007 | Gill | A61B 1/0607 600/112 |
| 2008/0183080 | A1 * | 7/2008 | Abraham | A61B 1/3132 600/466 |
| 2008/0188767 | A1 * | 8/2008 | Oaki | A61B 10/04 600/566 |
| 2009/0221873 | A1 * | 9/2009 | McGrath | A61B 1/00128 600/153 |
| 2009/0318798 | A1 * | 12/2009 | Singh | A61B 1/012 600/424 |
| 2010/0225424 | A1 * | 9/2010 | Yeates | H01P 11/003 333/238 |
| 2011/0245605 | A1 * | 10/2011 | Jacobsen | A61B 1/313 600/109 |
| 2011/0261183 | A1 * | 10/2011 | Ma | A61B 90/361 348/77 |
| 2012/0116209 | A1 * | 5/2012 | Klee | G01R 33/34084 600/411 |
| 2014/0039456 | A1 * | 2/2014 | Lerner | A61F 9/007 604/506 |
| 2015/0011891 | A1 * | 1/2015 | Yamada | H01R 12/598 600/466 |
| 2015/0031946 | A1 * | 1/2015 | Saadat | A61B 1/00087 600/104 |
| 2015/0150441 | A1 * | 6/2015 | Ouyang | A61B 10/04 600/109 |
| 2015/0196197 | A1 * | 7/2015 | Kienzle | A61B 17/3417 600/478 |
| 2015/0313634 | A1 * | 11/2015 | Gross | A61B 1/0676 606/185 |
| 2015/0342621 | A1 * | 12/2015 | Jackson, III | A61B 5/6848 600/546 |
| 2016/0081712 | A1 * | 3/2016 | Heniford | A61B 17/3474 600/424 |
| 2016/0174819 | A1 * | 6/2016 | Ouyang | A61B 1/00128 600/105 |
| 2016/0256670 | A1 | 9/2016 | Tepper et al. | |
| 2016/0353973 | A1 * | 12/2016 | Mirza | A61B 1/00108 |
| 2017/0209022 | A1 * | 7/2017 | Molnar | A61M 16/0465 |

* cited by examiner

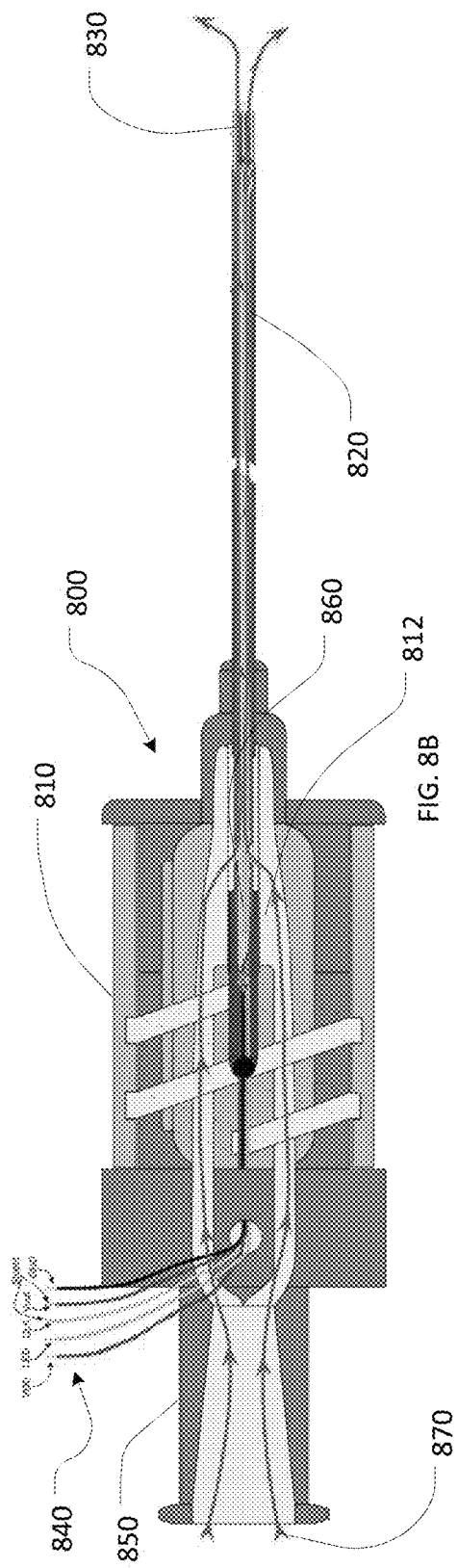

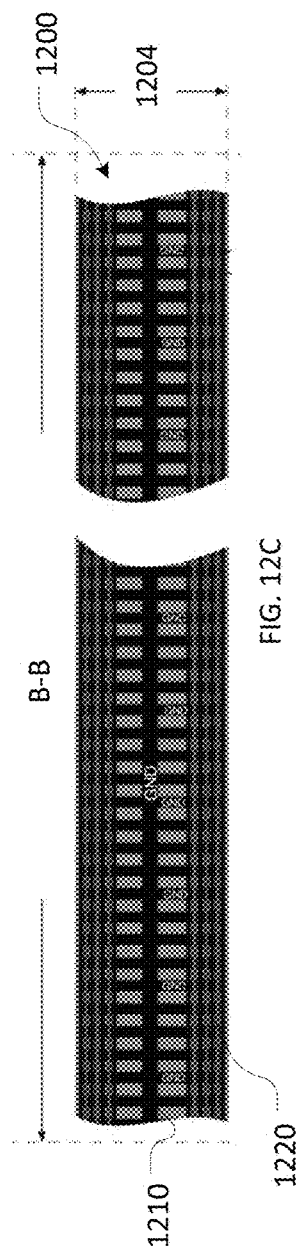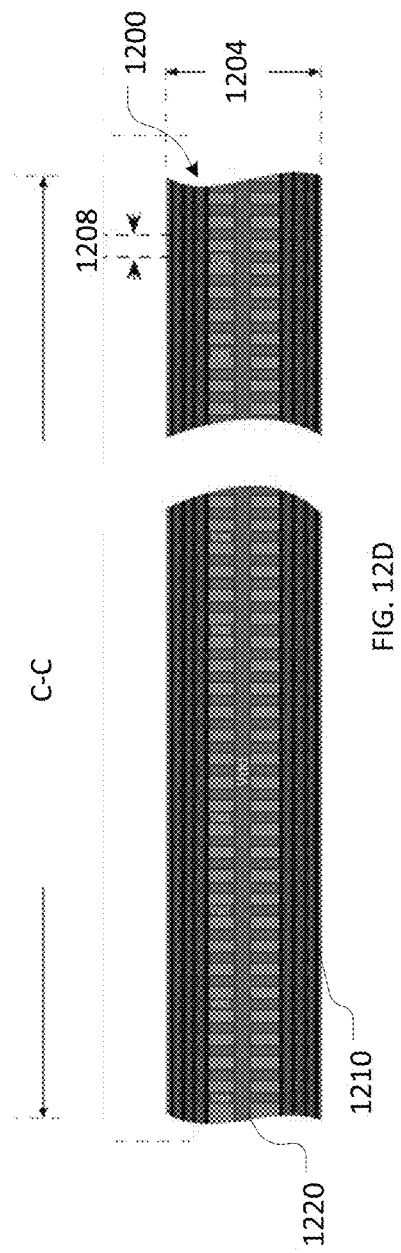

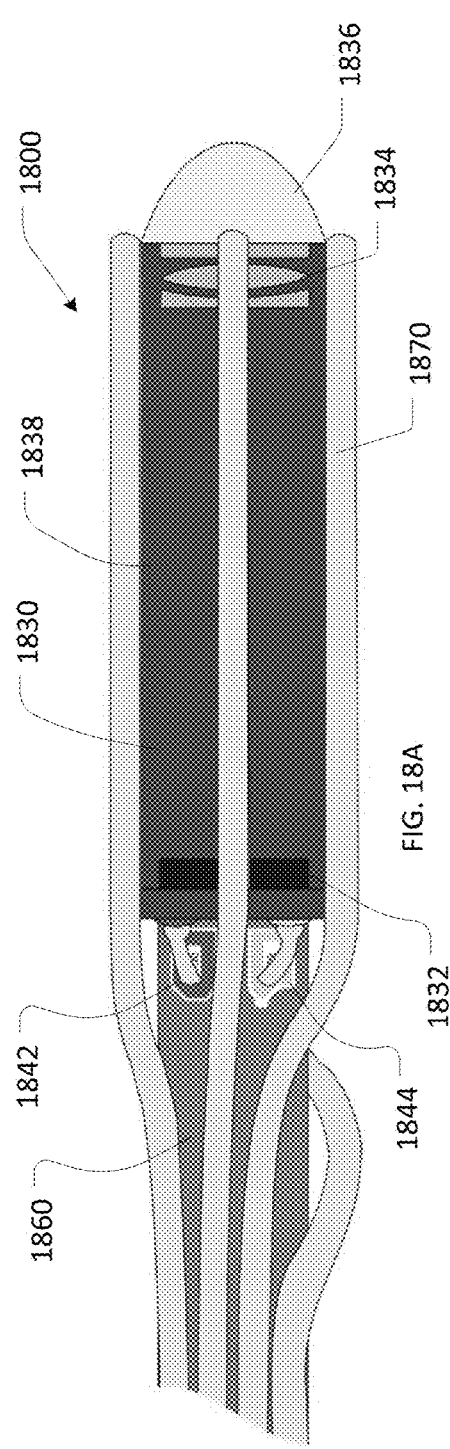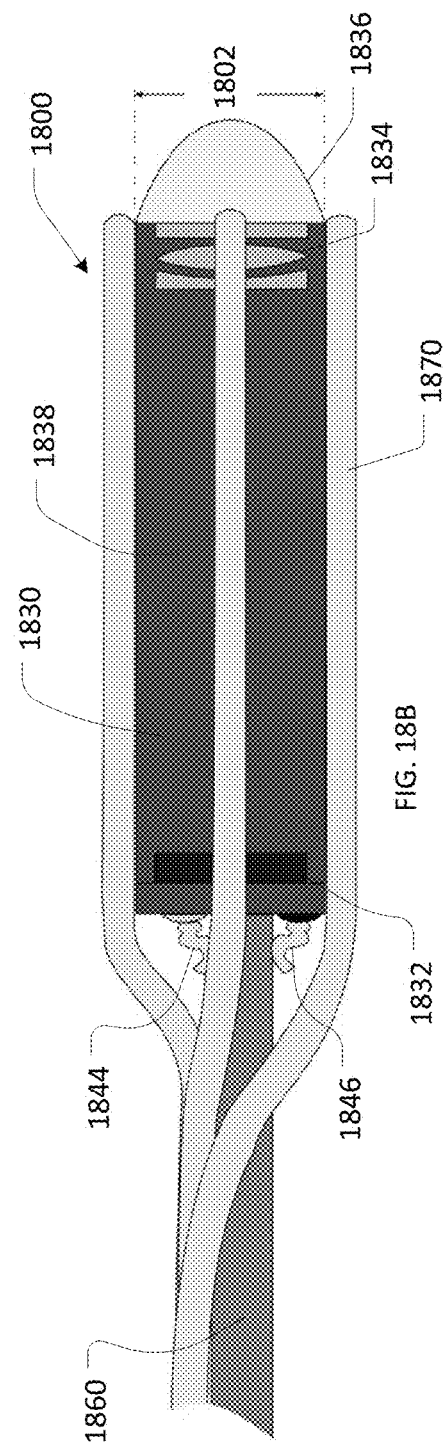

US 11,166,629 B2

VIDEO NEEDLE SYRINGE

CROSS REFERENCE TO RELATED APPLICATIONS

This application claims the benefit of U.S. Provisional Patent Application No. 62/401,784, filed on Sep. 29, 2016, which is incorporated by reference herein for all purposes.

BACKGROUND

Traditional surgical procedures are typically open procedures. In an open surgical procedure, a surgeon makes a large incision on a patient in order to view and correct physical ailments using surgical tools. Open procedures have several drawbacks. The large surgical incisions used to perform open procedures can become infected. Surgeons may damage surrounding tissues during open procedures, while trying to manipulate the surgical site. Open procedures often require patients to undergo full anesthesia, which independently increases risks of death and/or serious complications. In addition, open procedures can cause patients severe discomfort during recovery periods.

In order to avoid the complications of open procedures, surgeons have developed minimally invasive surgical techniques to perform surgeries that were traditionally performed as open procedures. In contrast to open procedures, minimally invasive procedures can be performed by inserting surgical tools through small incisions in a patient's skin. Minimally invasive procedures have various advantages over open procedures, including lower infection risks, lower patient discomfort, and lower anesthesia requirements.

The small incisions used in minimally invasive procedures make viewing the surgical field difficult. Accordingly, surgeons generally use imaging devices, e.g., endoscopes, during minimally invasive procedures in order to indirectly view the surgical field. Some of these imaging devices must be inserted into a patient's body through the small incisions.

Arthroscopy is a type of minimally invasive orthopedic procedure performed in a skeletal joint cavity. An arthroscope includes a camera that may be inserted directly into a skeletal joint. With help from the arthroscope, surgeons can diagnose various problems related to the skeletal joint.

In certain cases, arthroscopes can be used to determine whether a therapeutic material should be delivered to the skeletal joint. For example, a surgeon may use an arthroscope to determine whether to deliver a drug, stem cells, or anesthesia for a future procedure to the skeletal joint. Some of these therapeutic materials can be injected using a syringe and a needle.

The cameras used in medical applications, such as those used in arthroscopes, should be precise and have high resolution. However, traditional high-resolution imaging modalities may be expensive. Furthermore, these imaging modalities may be bulky, and unsuitable for certain applications.

SUMMARY

According to various embodiments of the present disclosure, an imaging apparatus includes a hub; a needle extending from the hub; a probe provided within the needle and configured to extend and retract; an imager disposed in the probe, the imager being configured to generate an imaging signal; and an interposer provided within the needle and including a substrate and a conductive line patterned on the substrate, the interposer being configured to receive the image signal from the imager via the conductive line.

In an embodiment, the imager includes a plurality of photocells configured to generate the imaging signal.

In an embodiment, the interposer includes first through third contacts, the first contact receiving the imaging signal from the imager, the second contact outputting an imager voltage to the imager, the third contact outputting a ground voltage to the imager, wherein a shielded line is coupled between the first contact and the imager.

In an embodiment, the shielded line includes a central line, a ground line, and an insulator disposed between the central line and the ground line, the ground line having a cross-hatched structure.

In an embodiment, the probe further includes: a cover, the cover being transparent; and a lens disposed between the imager and the cover, the lens being configured to focus light on the plurality of photocells.

In an embodiment, the apparatus further includes a lumen configured to hold fluid, the lumen extending through the hub and the probe, wherein the interposer is disposed inside of the lumen.

In an embodiment, the interposer is covered in a hydrophobic sealant.

In an embodiment, the apparatus further includes a fitting coupled to the hub, the hub being coupled between the fitting and the needle, the fitting being configured to form a fluid-tight seal with a pressure source, wherein the lumen extends through the fitting.

In an embodiment, the probe has one or more side ports coupled to the lumen, the one or more side ports being covered by the needle when the probe is in a first position, the one or more side ports being exposed when the probe is in a second position.

In an embodiment, the apparatus further includes a plurality of light pipes disposed between the probe and the needle; and a plurality of light sources optically coupled to the plurality of light pipes.

In an embodiment, the interposer includes a fourth contact and a fifth contact, the fourth contact outputting a voltage to the plurality of light sources, the fifth contact outputting a ground voltage to the plurality of light sources.

According to various embodiments, an imaging module includes an imager disposed in a probe of an imaging apparatus, the imager being configured to generate an imaging signal; and an interposer provided within a needle of the imaging apparatus, the interposer including a substrate and a conductive line patterned on the substrate, the interposer being configured to receive the image signal from the imager via the conductive line.

In an embodiment, the interposer includes first through third contacts, the first contact receiving the imaging signal from the imager, the second contact outputting an imager voltage to the imager, the third contact outputting a ground voltage to the imager, wherein a shielded line is coupled between the first contact and the imager.

In an embodiment, the shielded line includes a central line, a ground line, and an insulator disposed between the central line and the ground line, the ground line having a cross-hatched structure.

In an embodiment, the interposer is disposed inside of a lumen of the imaging apparatus, fluid flowing through the lumen.

In an embodiment, the interposer is covered in a hydrophobic sealant.

In an embodiment, the interposer includes a fourth contact and a fifth contact, the fourth contact outputting a voltage to a plurality of light sources, the fifth contact outputting a ground voltage to the plurality of light sources.

According to various embodiments of the present disclosure, a method includes applying a photoresist onto a substrate; forming a trench in the substrate by etching a portion of the substrate; and forming a conductive line by depositing a conductive material in the trench, wherein the line is configured to receive an imaging signal from an imager, the imager being disposed in a probe of a needle apparatus.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 8A through 8C illustrate fluid flow through an imaging needle apparatus according to various embodiments.

FIGS. 12A through 12D illustrate an interposer according to an embodiment.

FIGS. 18A through 18D illustrate an imaging apparatus according to an embodiment.

DETAILED DESCRIPTION

Figure 1A:
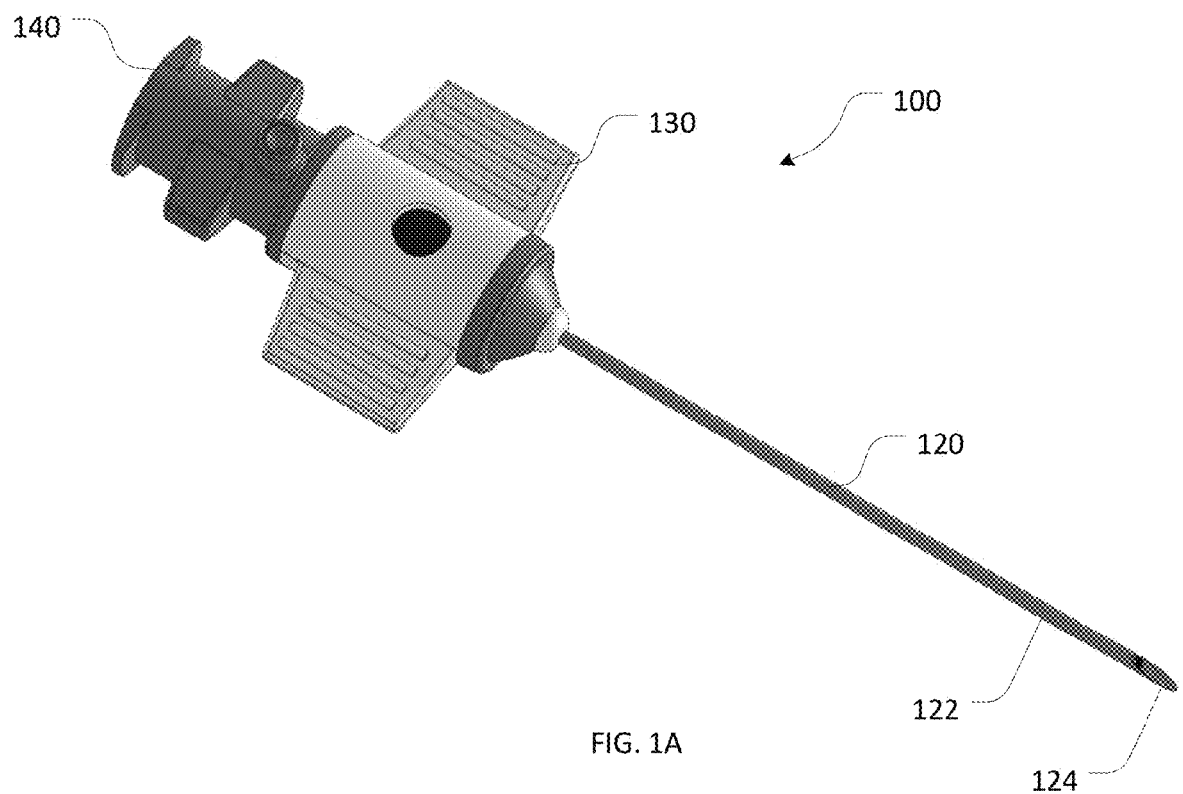
FIG. 1A illustrates an imaging needle apparatus when a probe tip provided within a needle according to an embodiment of the disclosure.

A detailed description of embodiments is provided below along with accompanying figures. The scope of this disclosure is limited only by the claims and encompasses numerous alternatives, modifications and equivalents. Although steps of various processes are presented in a particular order, embodiments are not necessarily limited to being performed in the listed order. In some embodiments, certain operations may be performed simultaneously, in an order other than the described order, or not performed at all.

Numerous specific details are set forth in the following description in order to provide a thorough understanding of the present disclosure. These details are provided for the purpose of example and embodiments may be practiced according to the claims without some or all of these specific details. For the purpose of clarity, technical material that is known in the technical fields related to this disclosure has not been described in detail so that the disclosure is not unnecessarily obscured.

Embodiments relate to an interposer, and an imaging needle apparatus including an interposer.

The imaging needle apparatus may be used as an arthroscope. Due to the small size of the imager in the imaging needle syringe, no positive pressure apparatus may be necessary to perform an arthroscopic procedure, unlike traditional arthroscopes. A user can use the imaging needle apparatus in an office setting, in order to provide a variety of injections.

The imaging needle apparatus may include a 21.5 G needle. The cutting edge of the needle may be covered or uncovered.

The video lens may be located on the tip of the imaging needle apparatus. The imaging needle apparatus may therefore be suitable for recording forward-viewing imaging and/or video recording through the lens. The lens may be extendable when, for example, the fins are twisted. The fins may be twisted along a direction circumferential to the needle. The lens may be locked in place, and the cutting edge of the needle may be covered when the video lens is extended.

The video lens allows users to easily navigate the tip of the needle into human joints and other spaces. When the video lens is inside a joint or space, the probe may be extended and the cutting edge of the needle may be actively covered or uncovered during a procedure.

A tip of the probe may be coated so that it can be easily located using ultrasound. The coating on the tip may also provide additional guidance during use.

The imager assembly may include a bee-eye imager, according to an embodiment of the present disclosure.

Once in place, the needle may be used for more precise targeting of fluids into imaged spaces. A retractable probe in the needle may include ports that can deliver injections of stem cells, platelet-rich plasma (PRP), biological glues or other materials with precision.

The imaging needle apparatus can be operated in various ways. For example, a user could place the tip into a patient's joint using the extended needle, image the joint using the imaging assembly, identify a meniscal tear or flap in the joint based on the imaged joint, and treat the meniscal tear or flap. The user may treat the meniscal tear or flap by gluing the tear or flap down, shave off at least a portion of the meniscal tear or flap, and/or inject stem cells/PRP through the needle into the joint, as the case dictates. The whole procedure may be easily recorded (e.g., by video) using the imaging assembly for documentation or future reference. Alternatively, the imaging needle apparatus can be used to image spaces in order to guide a second micro needle tool that can cut or otherwise manipulate tissues as needed.

The imaging needle apparatus according to embodiments of the present disclosure may be much smaller and even less invasive (i.e., more suited for minimally invasive procedures) than traditional instruments. In an embodiment, the small imager housed probe can be disposed inside of a relatively small needle, as compared to traditional instruments.

In addition, embodiments of the present disclosure may have many other applications besides orthopedics applications. Embodiments can be readily adapted to a broad variety of of scopes and catheters, and have a wide application to the many fields in medicine. For example, embodiments of the imaging needle apparatus could be used to further miniaturize cardiac catheters, which can allow safer intra-vascular navigation and placement. The imaging needle apparatus may also be used as, or may become, a much smaller laproscope.

In addition, embodiments of the present disclosure could be also used for needle guidance and tissue biopsies of all types. For example, the imaging needle apparatus may be inserted into a tissue, and allow a user to recognize and confirm tissue changes through the lens. Accordingly, the imaging needle apparatus can be used to more accurately biopsy tissue as needed.

The imaging needle apparatus, according to an embodiment, may be used to perform growingly important percutaneous procedures. According to an embodiment, the small size of the needle and forward viewing lens system may be used to assist all manner of office-based diagnostics and procedures.

Eventually, current open surgical procedures performed in a hospital setting may one day be easily and safely done without general anesthesia in an office procedure setting using embodiments of the imaging needle apparatus. Embodiments of the imaging needle apparatus will not only make procedures more convenient for both patients and doctors, but they could also significantly reduce patient risk and health costs.

Embodiments relate to an imaging needle apparatus. The imaging needle apparatus may have a body attached to a needle with a retractable tip. For example, the imaging needle may include a needle as well as a probe. The needle may be sufficiently sharp enough to pierce soft tissue, and the probe may be used to image the surrounding environment.

Either one of the needle and the probe may be retractable. When the probe extends beyond the sharp tip of the needle, the imaging needle apparatus may be blunt. When the sharp tip of the needle extends beyond the blunt tip of the probe, the imaging needle apparatus may be sharp.

The tolerances between the needle and the probe are such that a minimal amount of spacing is present to assure unimpeded protraction and retraction of the probe with respect to the needle. Such tight tolerances allow shielding of the outer sharp cutting edge when the probe is protracted.

The retraction operation can be performed via a control mechanism. The probe may be retracted and housed inside of the needle when the control mechanism is in a first state, and may be extended from the sharp tip of the needle when the control mechanism is in a second state. The control mechanism may be provided on the body.

The control mechanism may include, for example, fins that extend radially from the body. The control mechanism may be, for example, a hub including two fins that extend on opposite sides of the body. A user may perform the retraction by rotating the fins. For example, a plate or tab attached to the probe may rotate through a spiral track along an interior surface of the hub as the fins are rotated around a rotation axis that is parallel to the needle.

The fins may also be accompanied by an indicator that shows whether the imaging needle is in a retracted state. The indicator may display a color that is based on whether the imaging needle is retracted. Accordingly, the indicator can inform the user of whether the blunt tip of the probe extends beyond sharp tip of the needle when the retractable tip is not visible to the user.

In an embodiment, the imaging needle may be used solely as an imaging device, or may be used as an imaging device, and as a means to deliver fluid into a desired space. Fluid may flow through the needle according to pressure applied by the body of the imaging needle.

The fluid through the side ports may be used to clear the viewing field of debris or tissue. During viewing, fluid flow may occur through the lumen and the side ports by operating a pressure source coupled to the imaging needle.

The pressure source may exert pressure on the fluid using, for example, a syringe, a bulb, a pump, and/or a similar structure, which is coupled to a fitting disposed on the body of the imaging needle.

An imager in the probe may be used to image the surrounding environment through a transparent cover on the distal end of the probe. A distal end of the probe may be the farthest end of the probe from the body of the imaging needle apparatus. The imager may be disposed distal to the holes in the sides of the probe.

The diameter of the needle may be relatively small, because the imager can be relatively small. The imager may include one or more cables, a stack of ICs, an imager chip, one or more light pipes, and a lens. The imager may be a bee-eye imager apparatus. The imager may include an IC stack comprising a plurality of photocells, and a lens assembly. The lens assembly may include a Fresnel lens.

The one or more cables can transmit electrical signals between the imager and an external device, such as a device including a memory and one or more processors, a device including a display, a device providing a voltage source, or a combination thereof.

The stack of ICs may and the imager may be used to convert light signals into the usable electrical signals transferred through the one or more cables. The imager may correspond to a plurality of pixels. The resolution of the imager corresponds to the number of photocells and/or pixels in the imager.

The one or more light pipes may guide light to and from the cover of the probe. The light pipes may include illumination light pipes, which may transmit light through the cover in order to illuminate an area that is being imaged. The illumination light pipes may be disposed along the interior of the probe. The illumination light pipes may extend along an outer edge of the imager chip and the IC stack, and may be bundled with the one or more cables. The illumination light pipes may guide light from one or more LEDs.

The one or more light pipes may also include a focusing light pipe. The focusing light pipe may be disposed between the imager chip and the lens of the imager. The focusing light pipe may transmit focused light from the lens to the imager. The illumination light pipes may be disposed around an outer circumference of the focusing light pipe.

The lens may be disposed between the imager and the cover of the imaging needle apparatus. The lens may focus light onto the imager.

The cover may be disposed over the probe. The cover may be transparent, such that light from the illumination light pipes may be transmitted through the cover.

Embodiments of various features of the imaging needle apparatus are disclosed in IMAGING NEEDLE APPARATUS, U.S. application Ser. No. 15/261,743, VIDEO NEEDLE SYRINGE, U.S. application Ser. No. 15/444,180, and IMAGING NEEDLE APPARATUS, U.S. application Ser. No. 15/036,609, which are herein incorporated by reference.

According to various embodiments, fluid may also flow through a lumen within the probe, and through side ports at the tip of the probe. The side ports may be disposed in the cover of the probe, and may be between illumination light pipes in the probe. When the probe is retracted inside of the needle, for example, the side holes are covered, and the fluid may flow out of the needle at a relatively low flow rate. When the probe is extended, the side holes are exposed, and the fluid can freely flow out of the side holes.

In order to connect the circuitry within the apparatus to external devices, such as voltage sources and computers for image analysis, the cables can extend directly to circuits within the apparatus. However, when the apparatus includes relatively small imagers, the apparatus may be difficult to manufacture using the cables alone. Furthermore, the cables may become dislodged from the circuitry in the apparatus when fluid flows through the apparatus.

According to various embodiments, an interposer is connected between the cables and the internal circuitry of the imaging needle. For example, the interposer is coupled between the cables and a plurality of light sources and/or the imager.

The interposer includes relatively small lines and electrical contacts disposed in a semiconductor or insulative substrate. The lines and contacts are generated using photolithography. The interposer is relatively easy to manufacture, and can take up less space within the imaging needle apparatus than the bundle of cables itself. In addition, the interposer is easier to install between the bundle of cables and the internal circuitry of the imager needle.

Figure 1B:
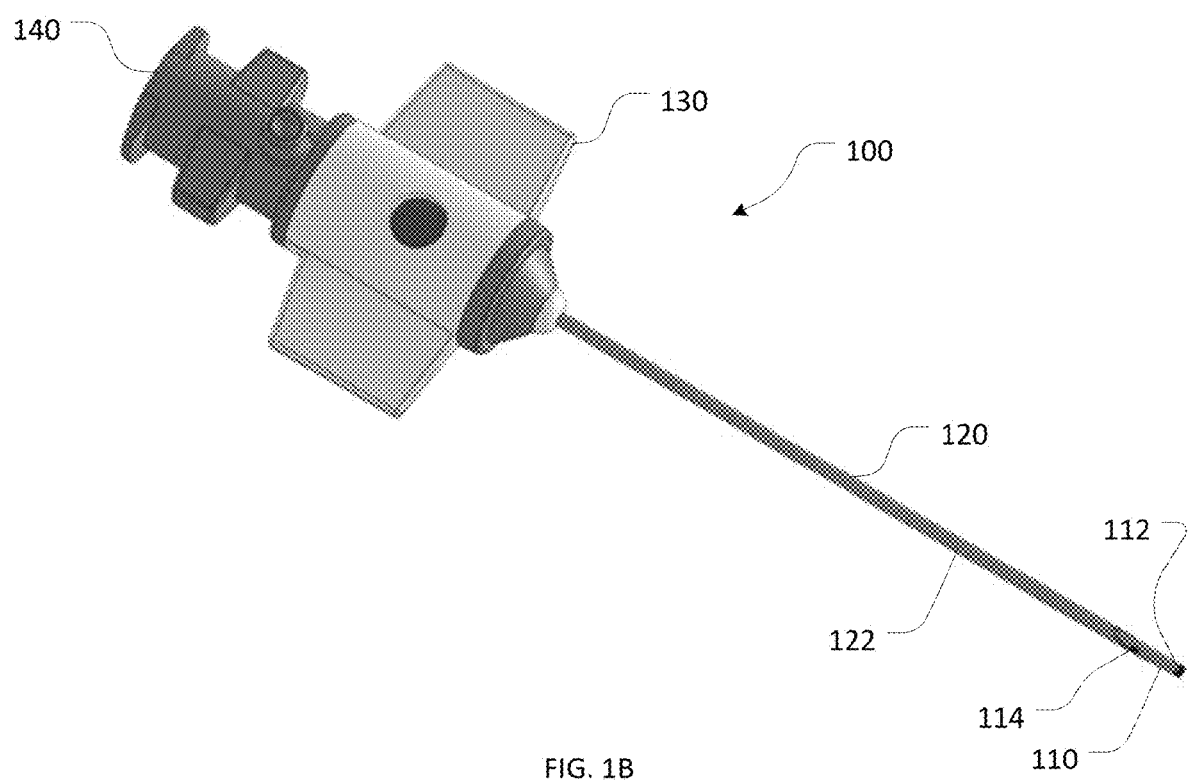
FIG. 1B illustrates the imaging needle apparatus of FIG. 1A when the probe tip is exposed according to an embodiment of the disclosure.

FIG. 1A illustrates an imaging needle apparatus when a probe tip provided within a needle according to an embodiment of the disclosure. FIG. 1B illustrates the imaging needle apparatus of FIG. 1A when the probe tip is exposed according to an embodiment of the disclosure. The imaging needle apparatus may be used to image a site, as well as to inject materials into the site.

In an embodiment, an imaging needle apparatus 100 includes a needle 120, a body 140 (e.g., a syringe), and a probe 110. The needle 120 includes a needle body or tube 122 (e.g., metallic tube having a circular cross-section) and a sharp tip 124. The probe 110 includes a tip 112 having a blunt front end.

In an embodiment, the needle 120 houses the probe 110, where the probe 110 may be housed within the needle 120 (see FIG. 1A) or exposed (see FIG. 1B) from the needle according to the modes of operation for the imaging needle apparatus. is In an embodiment, the probe 110 may be extended or retracted relative to the needle 110 based on an operation being performed by a user. For example, the imaging needle apparatus may retract the probe 110 into the needle 120 to use the sharp tip 124 of the needle to pierce tissues as needed.

Materials may be injected through the needle. The materials may be fluid, therapeutic materials, such as injectable drugs and/or cell suspensions. In an embodiment, the materials may be injected through a side port or hole 114 in the tip of the probe.

The body 140 (e.g., a hub connected to a syringe) may store the materials that can be injected through the needle, and may be used to exert pressure on the materials so that the materials are driven through the needle. The body 140 may include an output port used to connect imaging circuitry in the imaging needle apparatus to an external device, e.g., a device including a display screen.

The body 140 may include one or more fins 130. The fins 130 may be turned by a user around an axis parallel to the needle 120. The probe of the needle 120 may be selectively retracted by turning the fins 130. For example, FIG. 1A illustrates the fins 130 in a position corresponding to a retracted state of the probe, and FIG. 1B illustrates the fins 130 in a position corresponding to an extended state of the probe.

The body 140 may further include an indicator displaying whether the probe is extended or retracted. For example, the indicator may be circular and may be colored based on whether the probe is extended or retracted. In an embodiment, the indicator may be green when the probe is extended, and may be red when the probe is retracted. Because the indicator is located on the body 140, rather than the needle 120, a user can use the indicator to confirm whether the probe is retracted when the needle 120 is injected into an opaque material.

Figure 1C:
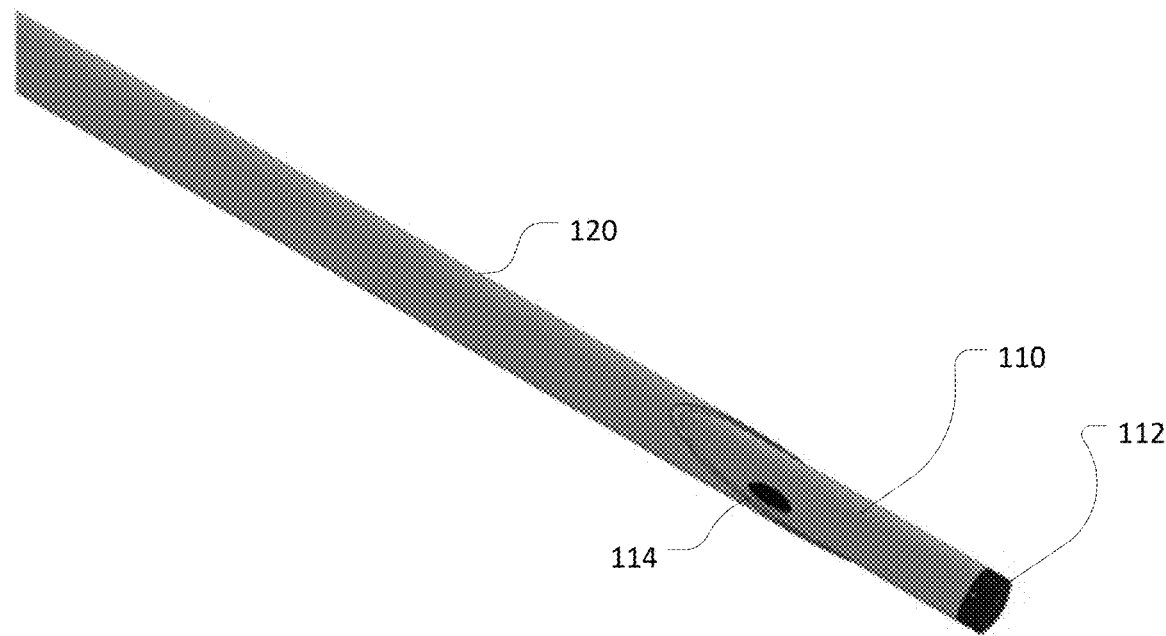
FIG. 1C illustrates a tip of the needle of FIGS. 1A and 1B according to an embodiment of the disclosure.

FIG. 1C illustrates a tip of the needle 120 of FIGS. 1A and 1B according to an embodiment of the disclosure. Specifically, FIG. 1C illustrates a probe 110 extending from the tip of the needle 120. As illustrated, the probe 110 is disposed inside of the needle 120.

An imaging apparatus may be disposed inside of the probe 110, and may image spaces pointing in an axial direction from the tip of the tip of the probe 110. That is, the imaging apparatus may point through the tip of the probe 110, which may be covered.

Materials injected through the needle 120 may be injected from the probe 110. Specifically, the materials may be injected through the one or more side ports 114 on an outer circumferential surface of the probe 110. When the probe 110 is extended, the side ports 114 of the probe 110 may be exposed. Accordingly, the materials may be injected into a space simultaneously while imaging the space.

Figure 2A:
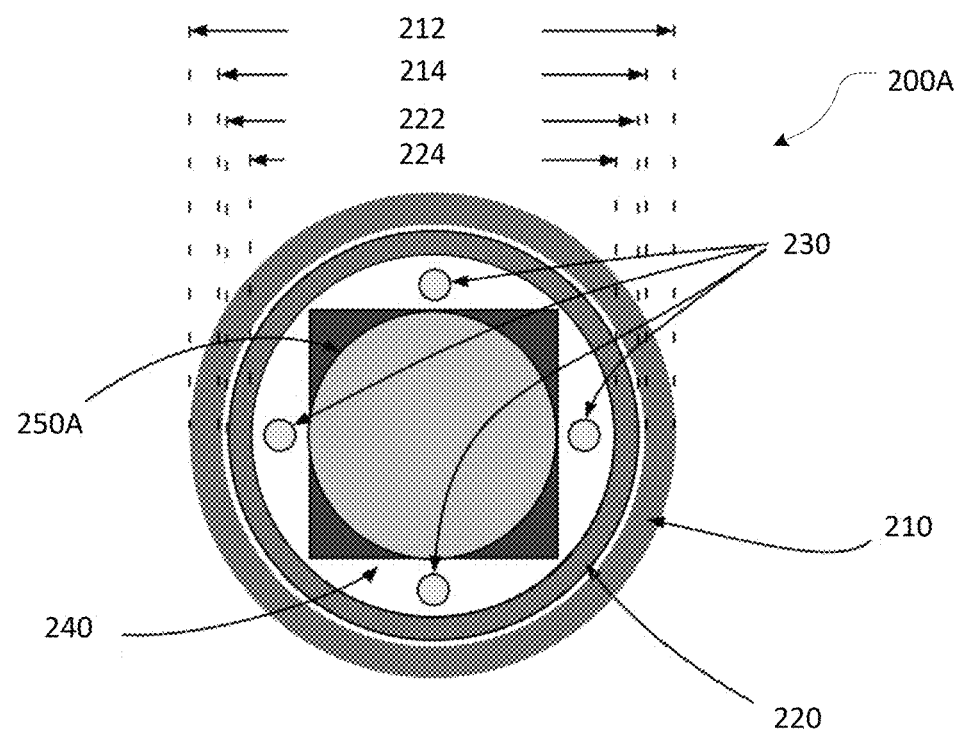
FIGS. 2A and 2B illustrate cross sections of imaging needle apparatuses from a tip view according to an embodiment of the disclosure.
Figure 2B:
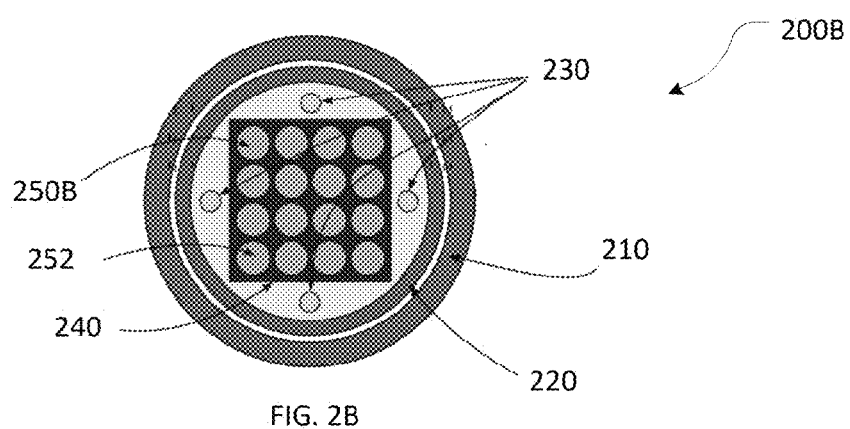

FIGS. 2A and 2B illustrate cross sections of imaging needle apparatuses from a tip view according to an embodiment of the disclosure.

The imaging needle apparatus 200A of FIG. 2A may include an outer cover 210, an inner cover 220, a plurality of light pipes 230, an imager 240, and a lens 250A. The imaging needle apparatus may further include a cover (not illustrated) covering the tip of the imaging needle apparatus.

The outer cover 210 may have a circular cross-section. In an embodiment, the outer cover 210 may correspond to a 21 gauge needle, with an outer diameter 212 of 819 microns, and with an inner diameter 214 of 700 microns.

The inner cover 220 may have a circular cross-section. In an embodiment, the inner cover 220 may correspond to a 22.5 gauge needle, with an outer diameter 222 of 667 microns and an inner diameter 224 of 579 microns.

The plurality of light pipes 230 may be disposed between an inner wall of the inner cover 220 and the imager 240. The plurality of light pipes 230 may extend down the length of the imaging needle apparatus. The plurality of light pipes 230 may emit light from the tip of the imaging needle apparatus, which may illuminate a target area that can be imaged by the imager 240. In an embodiment, the plurality of light pipes 230 may be coupled to one or more LEDs. In an embodiment, each of the plurality of light pipes 230 may have a diameter of 50 microns.

The imager 240 may be disposed inside of the inner cover 220 and may be covered by the lens 250A. The imager 240 may have a different shape than the inner surface of the inner cover 220. According to various embodiments, the imager 240 includes a plurality of photocells that generate imaging signals. In an embodiment, the imager has a square, 400 micron by 400 micron cross-section.

The lens 250A may focus light onto the imager 240. The lens 250A may be a single, cylindrical structure. In an embodiment, the lens 250A may have a different cross-sectional shape than the imager 240.

The imaging needle apparatus 200B of FIG. 2B is similar to the imaging needle apparatus 200A of FIG. 2A. However, the imaging needle apparatus of FIG. 2B includes a lens assembly 250B in place of the lens 250A. The lens assembly 250B may include a plurality of individual lenses 252 that respectively focus light onto the imager 240. In an embodiment, each of the plurality of lenses 252 may focus light on one of the photocells of the imager 240. The lens assembly 250B may be a Fresnel lens, and the lens assembly 2650B and the imager 2640 may be part of a bee-eye imager.

In an embodiment, each of the plurality of lenses 2652 may have a diameter of 85 microns.

Figure 3A:
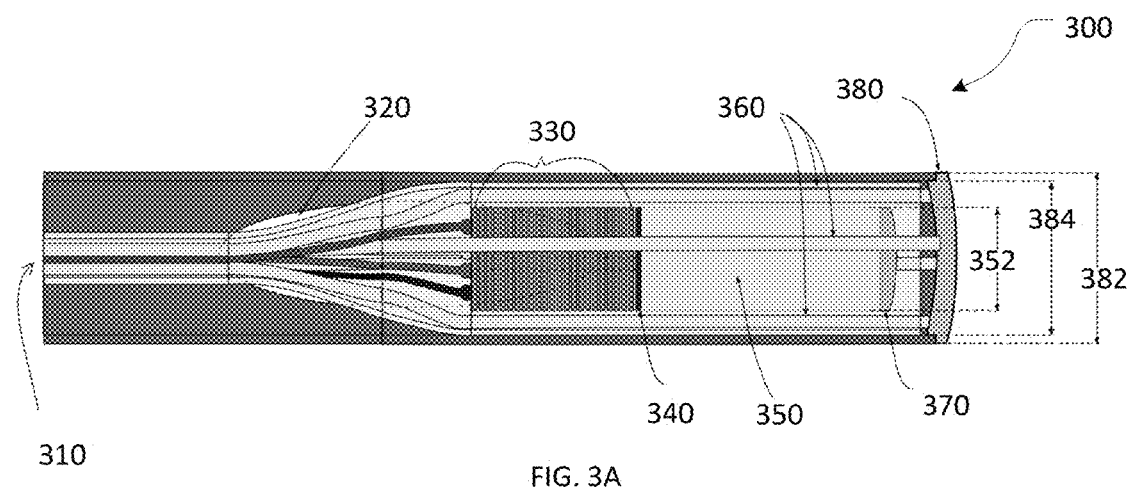
FIG. 3A illustrates a probe of an imaging needle apparatus according to an embodiment of the disclosure.
Figure 3B:
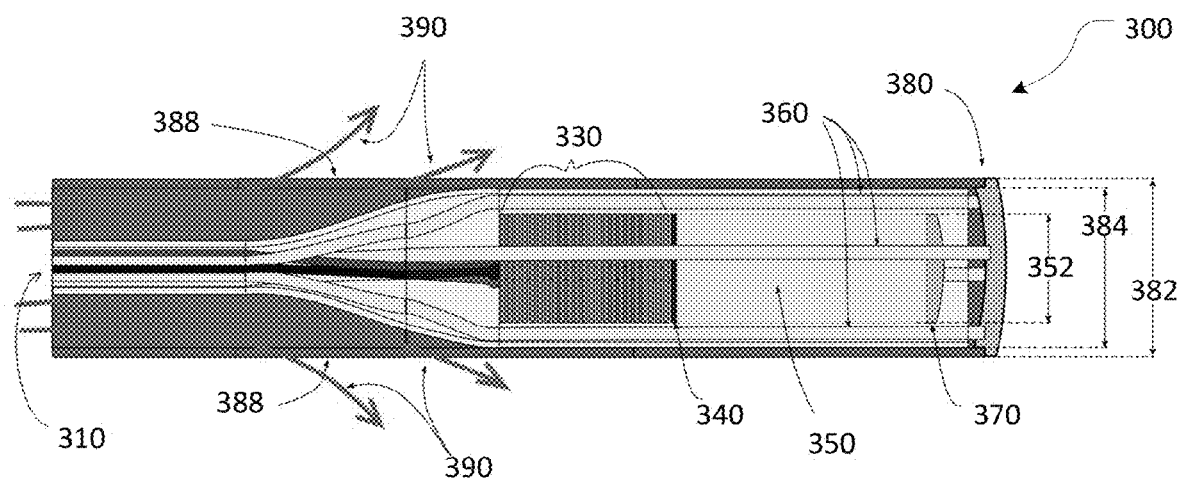
FIG. 3B illustrates the probe of FIG. 3A emitting fluid according to an embodiment of the disclosure.

FIG. 3A illustrates a probe 300 of an imaging needle apparatus according to an embodiment of the disclosure. FIG. 3B illustrates the probe 300 of FIG. 3A emitting fluid according to an embodiment of the disclosure.

The probe 300 includes a bundle 310, a side port opening 320, a stack 330, an imager chip 340, a focusing light pipe 350, a plurality of illumination light pipes 360, a lens 370, and a cover 380.

The bundle 310 may include a plurality of cables and the plurality of illumination light pipes 360. The plurality of cables may be micro USB cables. In an embodiment, each of the cables may include a 25 micron gold or silver core with a 2.5 micron layer of insulation around the gold or silver core. The bundle 310 may extend from the stack 330. The bundle 310 may transmit light through the illumination light pipes 360 and transmit imaging signals from the stack 330.

The side port opening 320 may be a hole in the cover 380. Materials may be injected to a target space through the side port opening 320. For example, a fluid 390 may be injected through the side port opening 320.

The stack 330 may produce imaging signals based on electrical signals produced by the imager chip 340. The stack 330 may include a plurality of ICs. The stack 370 and the imager chip 330 may be part of an imager, for example, a bee-eye imager.

The imager chip 340 may receive light and produce electrical signals based on the received light. These electrical signals are also referred to as "imaging signals." The imager chip 340 may be stacked on the stack 330, and may be electrically coupled to the stack 330. The imager chip 340 may be disposed between the stack 330 and the focusing light pipe 350. The imager chip 340 may include a plurality of photocells, corresponding to a plurality of pixels.

The focusing light pipe 350 may channel light from the lens 370 to the imager chip 340.

The plurality of illumination light pipes 360 may be used to transmit light from the probe to an external area to be imaged. The plurality of illumination light pipes 360 may extend from the bundle 310, and along outer walls of the stack 330, the imager chip 340, and the lens 370. The plurality of illumination light pipes 360 may be fiber optic cables.

The lens 370 may focus light received by the probe to the imager chip 340.

The cover 380 may be disposed around the probe. The cover 380 may emit materials through the side port, which may be located between a body and the stack 330. Accordingly, the fluid 390 may not flow between the cover 380 and the stack 330, the imager chip 340, the focusing light pipe 350, and the lens 370. The cover 370 may have a sidewall 388 and a transparent cap. Light from the plurality of illumination light pipes 360, and light to the lens 370, may flow through the transparent cap.

In an embodiment, the cover 380 may have an outer diameter of 0.667 mm, an inner diameter of 0.592 mm, and the lens 370 may have a diameter of 0.400 mm.

Figure 4A:
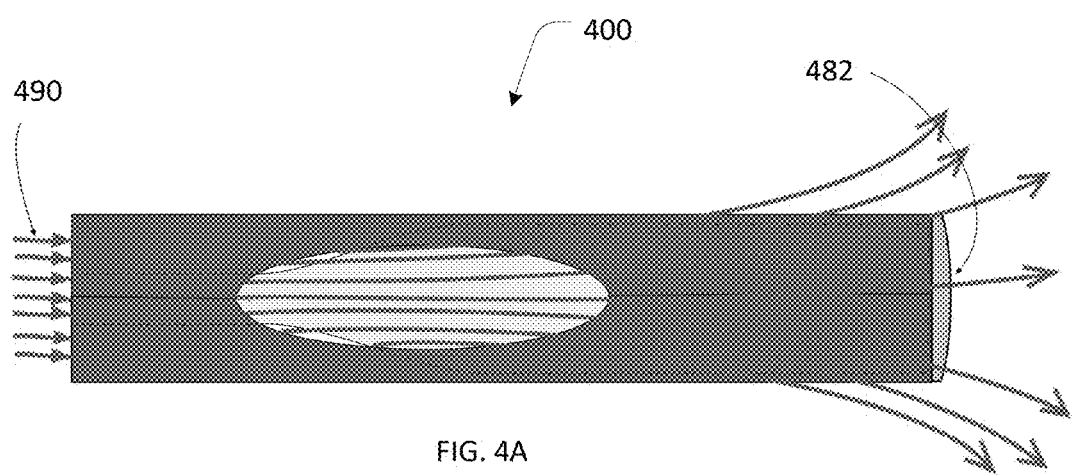
FIG. 4A illustrates a fluid flow diagram of a probe according to an embodiment of the disclosure.

FIG. 4A illustrates a fluid flow diagram of probe 400 according to an embodiment of the disclosure. Fluid 490 may be injected through a needle and through a side port in a cover 482 of the probe 400.

Figure 4B:
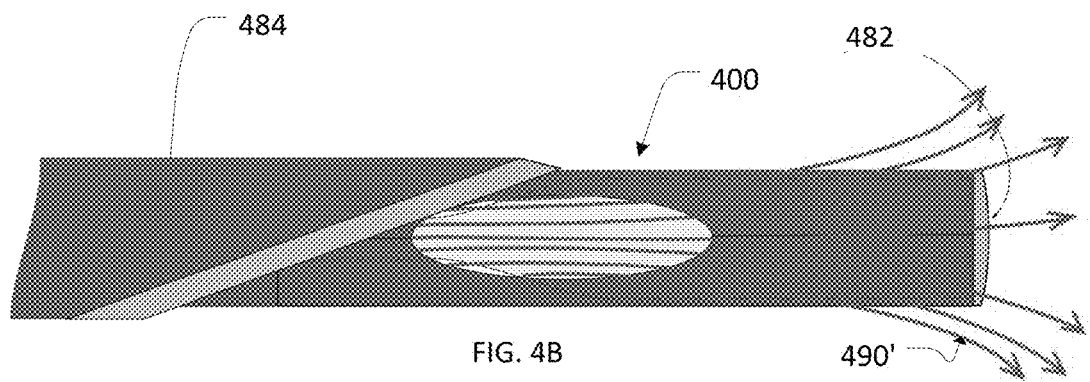
FIG. 4B illustrates fluid flow diagram of the probe when the probe is partially covered with a needle according to an embodiment of the disclosure.

FIG. 4B illustrates fluid flow diagram of the probe 400 when the probe 400 is partially covered with a needle 484 according to an embodiment of the disclosure. When the probe 400 is extended, a side port in a cover 482 of the probe may be uncovered. Accordingly, fluid 490' may flow from the side port without being inhibited by the needle 484.

FIGS. 5A through 7D illustrate an imaging needle apparatus 500 according to an embodiment.

The imaging needle apparatus 500 includes a hub 510, a needle 520, a probe 530, a plurality of cables 540, a fitting 550, and an interposer 560.

The hub 510 is configured to extend or withdraw the probe 530 with respect to a tip of the needle 520 by moving a plate 512. In an embodiment, the hub 510 includes a plurality of fins that are rotatable around a central axis of the imaging needle apparatus 500. The plate 512 is located at a position along the axis corresponding to a current extended state of the probe 530. The plate 512, for example, moves along a spiral track inside of the hub 510.

The needle 520 extends from the hub 510 in a direction of the axis, and is disposed over the probe 530. In an embodiment, the needle 510 has a tip that is sharp and can pierce soft tissue. When the probe 530 is retracted, the tip of the needle 510 is exposed.

The probe 530 extends from the hub 510 in the direction of the axis, and is disposed inside of the needle 520. According to various embodiments, the probe 530 includes one or more lenses, one or more light guides, one or more light sources (e.g., LEDs) respectively coupled to the one or more light guides, an imager, an outer shell, and a lens cover. The probe 530 is therefore configured to image an environment adjacent to the apparatus 500. In an embodiment, the imager images a space in front of the tip of the needle 520.

In an embodiment, the probe 530 also includes a lumen and one or more side ports. Fluid can be injected into a space defined by the lumen via a source coupled to the fitting 550, and may flow out of the one or more side ports. When the probe 530 is fully retracted, the one or more side ports are covered by the needle 520. When the probe 530 is fully extended, the one or more side ports are fully exposed. The probe 530 is therefore configured to inject desired fluids into a target space.

The plurality of cables 540 electrically connect the apparatus 500 to an external source. The plurality of cables 540 are electrically connected to the interposer 560. The plurality of cables 540 includes an imager voltage cable VDD, an LED voltage cable LED, a clock cable CLK, an imager output cable Vout, and a ground cable GND.

The imager voltage cable VDD is electrically connected between a first voltage source and the imager in the probe 530. The imager voltage cable VDD supplies the imager with voltage for operation.

The LED voltage cable LED is electrically connected between a second voltage source and the one or more LEDs in the probe 530. In an embodiment, the LED voltage cable LED carries a DC voltage used to operate the LEDs. The voltage supplied by the second voltage source is different than the voltage supplied by the first voltage source, for example.

The clock cable CLK carries a clock signal to the interposer 560.

The imager output cable Vout outputs imaging signals from the imager. In an embodiment, the imager output cable Vout is connected to a computer, which can be used to analyze the imaging signals from the imager.

The ground cable GND carries a ground voltage to the interposer 560.

According to various embodiments, one or more of the plurality of cables 540 are shielded. For example, the clock cable CLK and the imager output cable Vout are shielded cables. The shielded cables prevent distortion of high-frequency electrical signals conducted through the cables.

The fitting 550 is configured to connect the apparatus 500 to a fluid and/or pressure source. The fitting 550 forms a fluid-tight seal with the fluid and/or pressure source. The fitting 550 includes, for example, a luer lock fitting configured to attach to a syringe. The fitting 500 includes a space defined by a lumen that connects to the space defined by the lumen of the probe 530. Accordingly, the fitting 550 is configured to conduct fluid from the fluid and/or pressure source into the probe 530.

The interposer 560 electrically connects the plurality of cables 540 to internal circuitry in the probe 530. For example, the interposer 560 connects to the imager and the one or more LEDs of the probe 530. In an embodiment, the interposer 560 is disposed inside of the space defined by the lumen of the probe 530, and is covered with a polymer seal to prevent fluid inside of the space from physically and/or electrically interfering with the interposer 560.

Figure 5A:
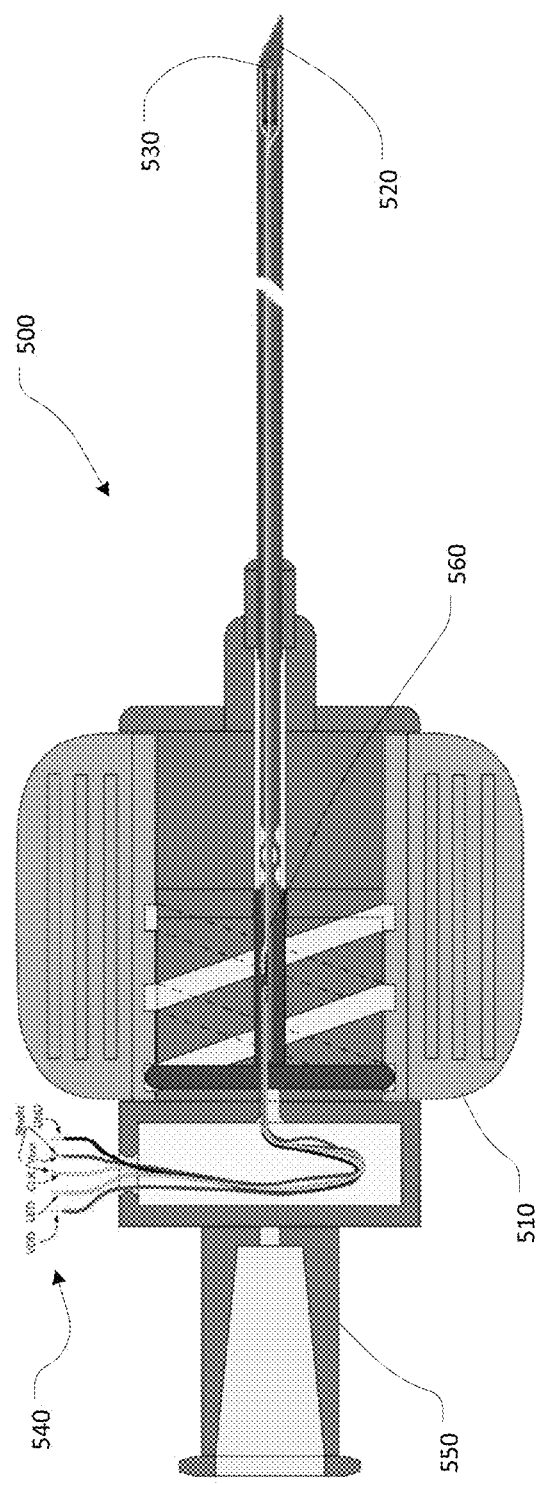
FIGS. 5A through 5D illustrate an apparatus when a probe is fully retracted, according to an embodiment.
Figure 5B:
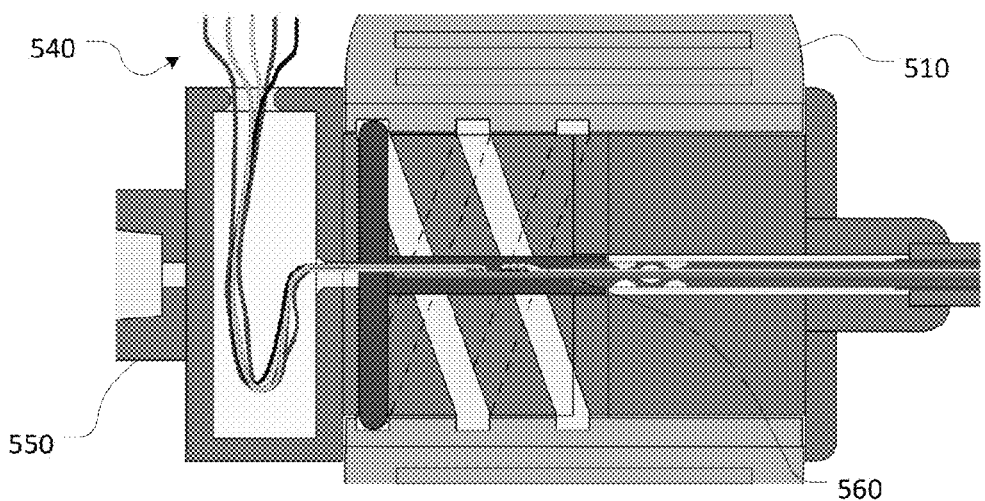
Figure 5C:
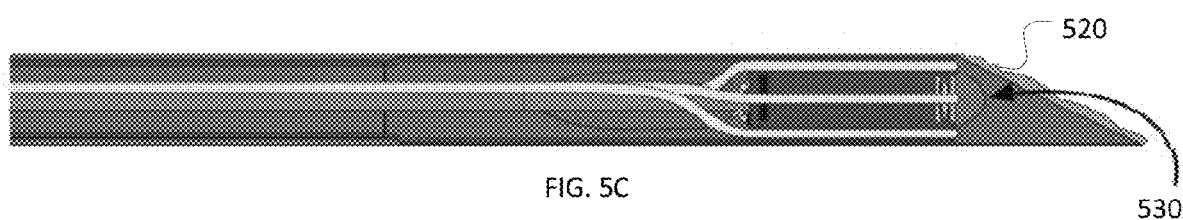
Figure 5D:
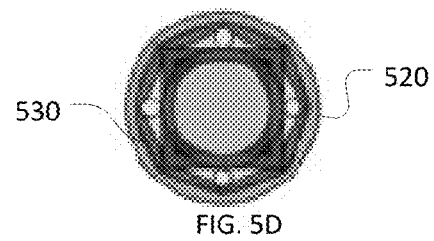

FIGS. 5A through 5D illustrate the apparatus 500 when the probe 530 is fully retracted, according to an embodiment. FIG. 5A illustrates a cross-section of the apparatus 500 along the axis. FIG. 5B illustrates a cross-section of the hub 510 along the axis. FIG. 5C illustrates a cross section of the needle 520 and the probe 530 along the axis. FIG. 5D illustrates a view of the apparatus 500 from the tip of the needle 520.

As illustrated in FIGS. 5A through 5D, a tip of the needle 520 extends beyond an end of the probe 530 when the probe 530 is fully retracted. The hub 510 is disposed at a 0 degree angle, and the plate 512 is located in a first position along the track.

Figure 6A:
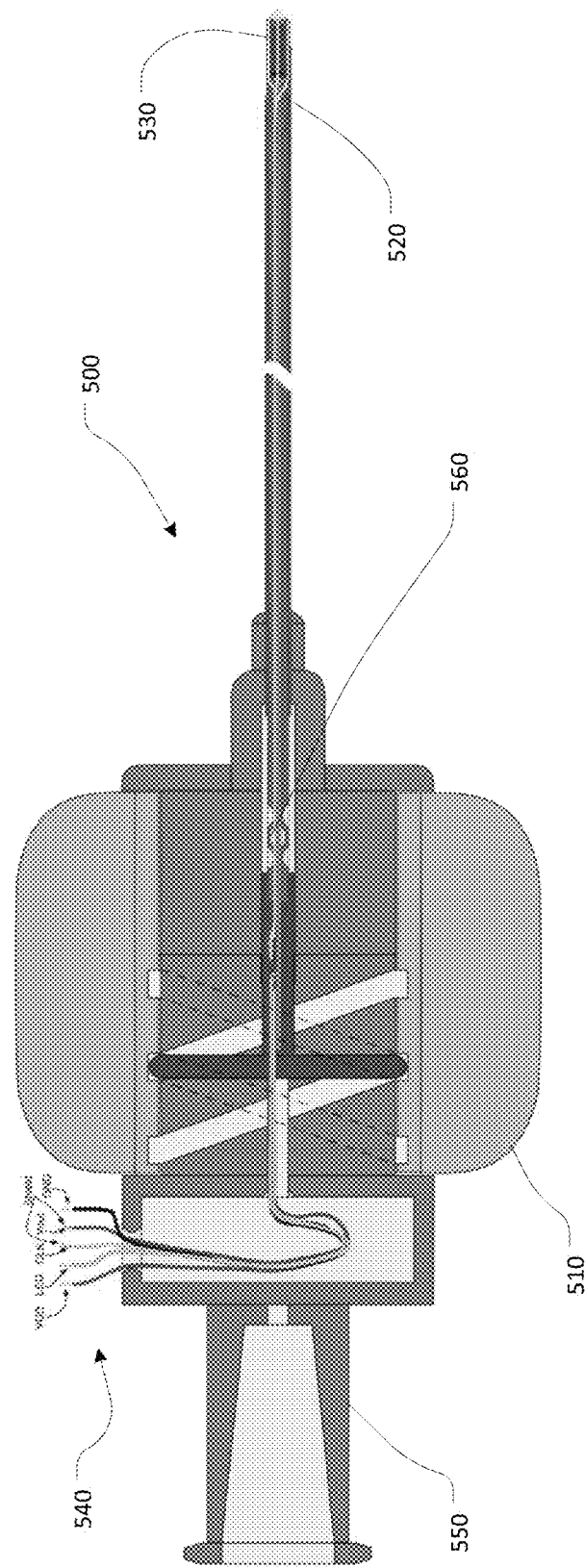
FIGS. 6A through 6D illustrate an apparatus when a probe is partially extended, according to an embodiment.
Figure 6B:
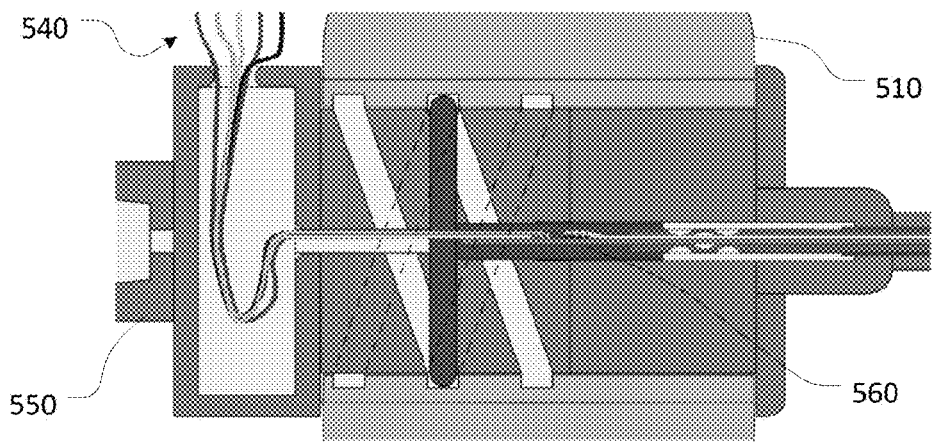
Figure 6C:
Figure 6D:
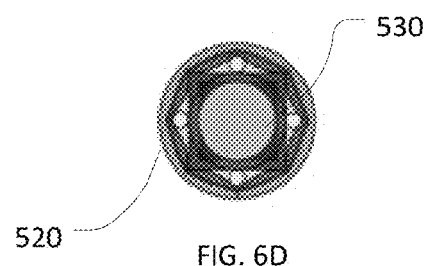

FIGS. 6A through 6D illustrate the apparatus 500 when the probe 530 is partially extended, according to an embodiment. FIG. 6A illustrates a cross-section of the apparatus 500 along the axis. FIG. 6B illustrates a cross-section of the hub 510 along the axis. FIG. 6C illustrates a cross section of the needle 520 and the probe 530 along the axis. FIG. 6D illustrates a view of the apparatus 500 from the tip of the needle 520.

As illustrated in FIGS. 6A through 6D, a tip of the needle 520 is even with an end of the probe 530, such that the tip of the needle 520 does not extend beyond the end of the probe 530. The hub 510 is disposed at a 180 degree angle, and the plate 512 is located in a second position along the track.

Figure 7A:
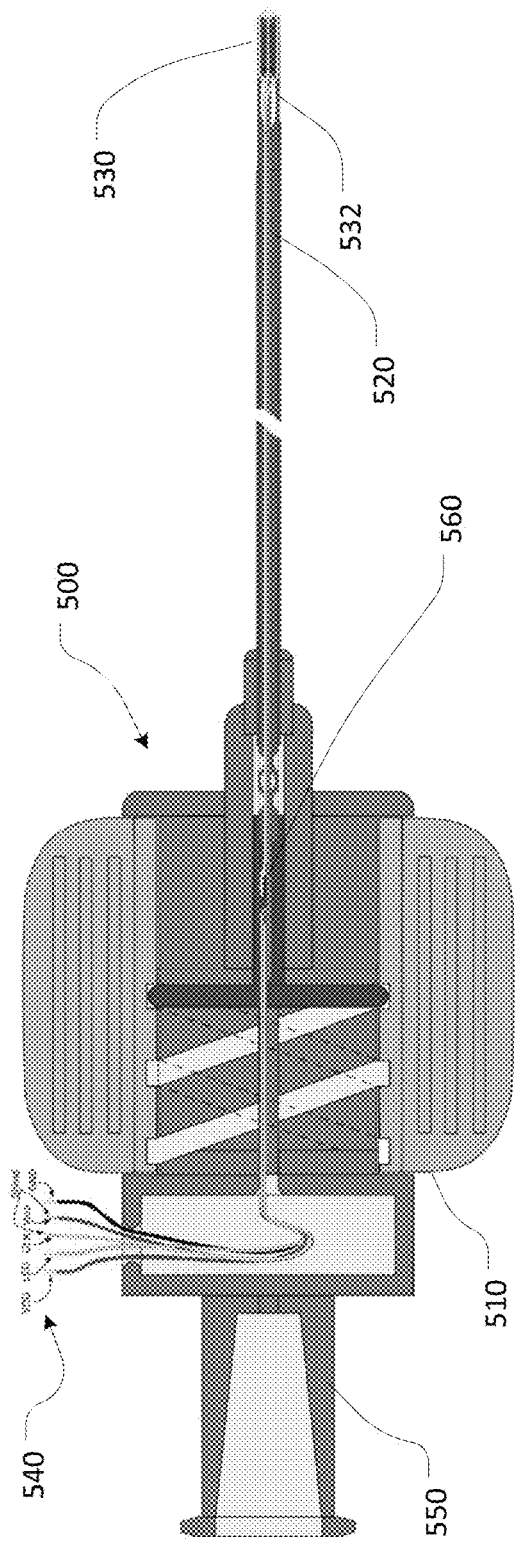
FIGS. 7A through 7D illustrate an apparatus when a probe is partially extended, according to an embodiment.
Figure 7B:
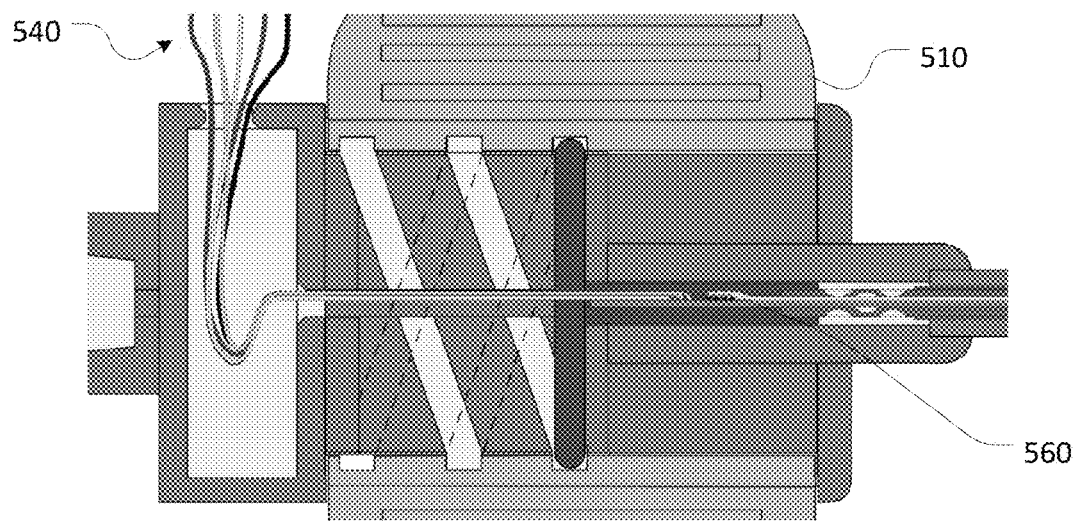
Figure 7C:
Figure 7D:
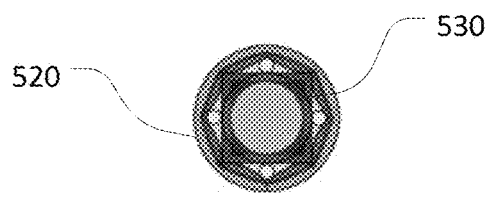

FIGS. 7A through 7D illustrate the apparatus 500 when the probe 530 is partially extended, according to an embodiment. FIG. 7A illustrates a cross-section of the apparatus 500 along the axis. FIG. 7B illustrates a cross-section of the hub 510 along the axis. FIG. 7C illustrates a cross section of the needle 520 and the probe 530 along the axis. FIG. 7D illustrates a view of the apparatus 500 from the tip of the needle 520.

FIGS. 7A through 7D show the end of the probe 530 extending beyond the tip of the needle 520, such that side ports 532 of the probe 530 are exposed. The hub 510 is disposed at a 360 degree angle, and plate 512 is located in a third position along the track.

Figure 8A:
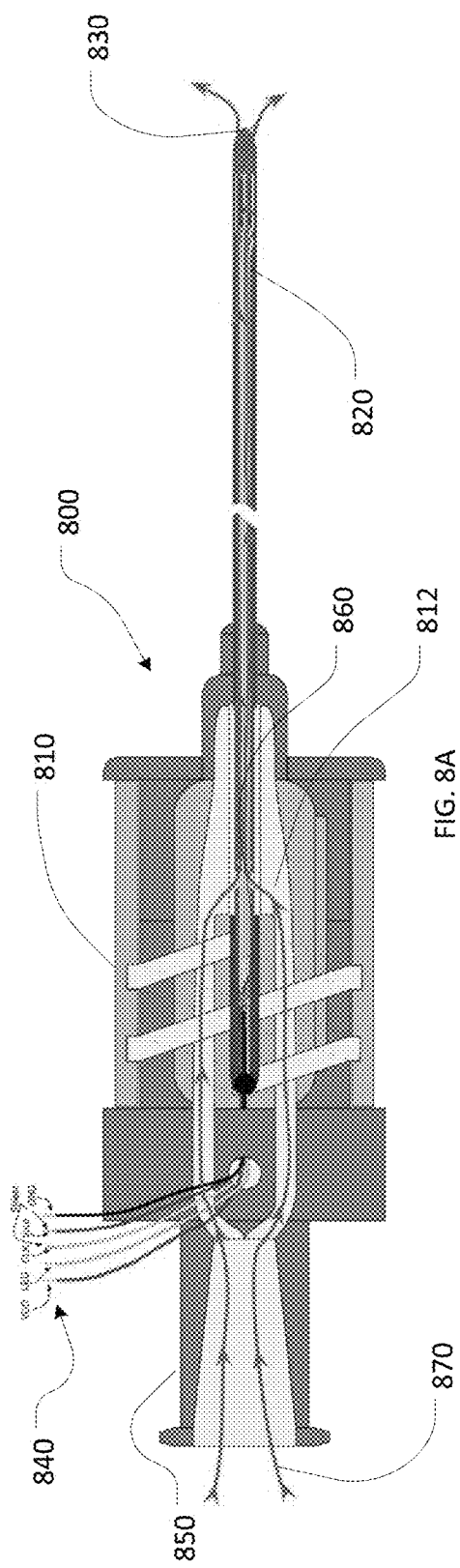
Figure 8C:
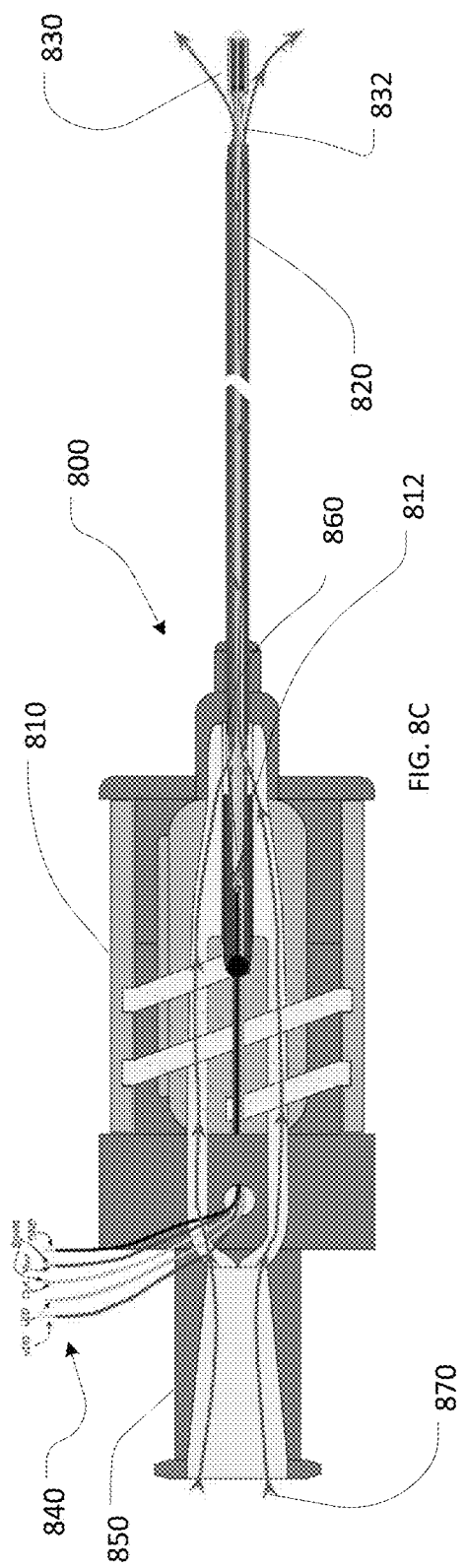

FIGS. 8A through 8C illustrate fluid flow through an imaging needle apparatus 800 according to various embodiments.

The imaging needle apparatus 800 includes a hub 810, a lumen 812, needle 820, a probe 830, a plurality of cables 840, a fitting 850, and an interposer 860. The lumen 812 extends through the hub 810, the probe 830, and the fitting 850. The interposer 860 is disposed in the lumen 812.

A fluid 870 enters the lumen 812 via the fitting 850. The fluid 870 flows through the lumen 812 from the fitting 850 into the hub 810, and then into the probe 830. In an embodiment, the lumen 812 diverts into one or more channels in the hub 810 and around the interposer 860. In certain embodiments, the interposer 860 is disposed in the lumen 812.

The fluid 870 exits the lumen 812 through one or more ports 832 of the probe 830. According to various embodiments, the ports 832 are side ports extending through a side wall of the probe 830 at a distal end of the probe 830.

FIG. 8A illustrates fluid flow through the apparatus 800 when the probe 830 is fully retracted from the tip of the needle 820. When the probe 830 is fully retracted, the fluid 870 exits the lumen 812 into a space between the probe 830 and the needle 820. The fluid 870 then flows out of the needle 820.

In an embodiment, the fluid 870 flow rate is controlled by the space between the probe 830 and the needle 820. Accordingly, a user may choose to inject the fluid 870 into a desired space as the probe 830 is retracted when a relatively low flow rate is desired.

FIG. 8B illustrates fluid flow through the imaging needle apparatus 800 when the probe 830 is partially extended according to an embodiment. When the probe 830 is partially retracted, the fluid 870 exits the lumen 812 inside of the needle 820.

FIG. 8C illustrates fluid flow through the imaging needle apparatus 800 when the probe 830 is fully extended according to an embodiment. When the probe 830 is fully extended, one or more side ports 832 of the probe 830 are exposed. The fluid 870 flows out of the probe 830 through the exposed side ports 832.

Figure 9A:
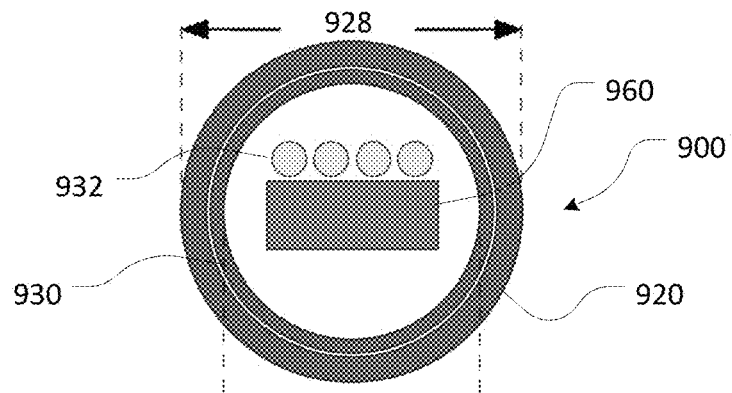
FIGS. 9A and 9B illustrate cross-sections of a needle apparatus according to an embodiment.
Figure 9B:
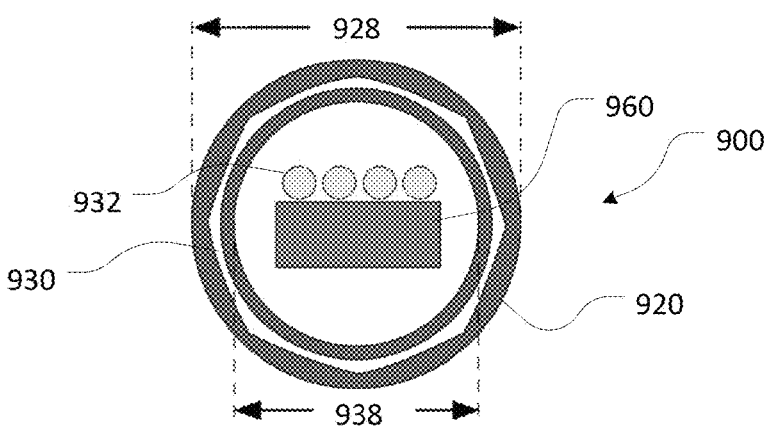

FIGS. 9A and 9B illustrate cross-sections of a needle apparatus 900 according to an embodiment.

FIG. 9A illustrates a cross-section of the apparatus 900 at a position adjacent to a hub from which a needle 920 and a probe 930 extend, according to an embodiment. An interposer 960 and a plurality of light pipes 932 are disposed in a space within the probe 930. An outer diameter of the needle 928 is longer than an inner diameter of the probe 938. An inner surface of the needle 920 conforms to an outer surface of the probe 930. A small space is disposed between the needle 920 and the probe 930. In an embodiment, a cross-section of the inner surface of the needle 920 is circular.

In an embodiment, fluid flows in the space around the interposer 960 and the plurality of light pipes 932. The interposer 960 is covered with a sealant in order to prevent the fluid from physically or electrically interfering with the interposer 960. For example, the interposer 960 is covered with a hydrophobic coating, such as NANOSLIC, a hydrophobic and oleophobic coating that is resistant to water, oils, and other liquids. In a specific example, a thickness of the hydrophobic coating, as applied, is 0.2 um to 4 um.

FIG. 9B illustrates a cross-section of the apparatus 900 at a position adjacent to a tip of the needle 920 and a tip of the probe 930 according to an embodiment.

As shown in FIG. 9B, a cross-section of an inner surface of the needle 920 has a polygonal shape. The polygonal shape is configured to provide a larger space between the needle 920 and the probe 930, than the circular shape illustrated in FIG. 9A.

An inner surface of the needle 920 therefore changes along the center axis of the apparatus 900, according to various embodiments.

Figure 10A:
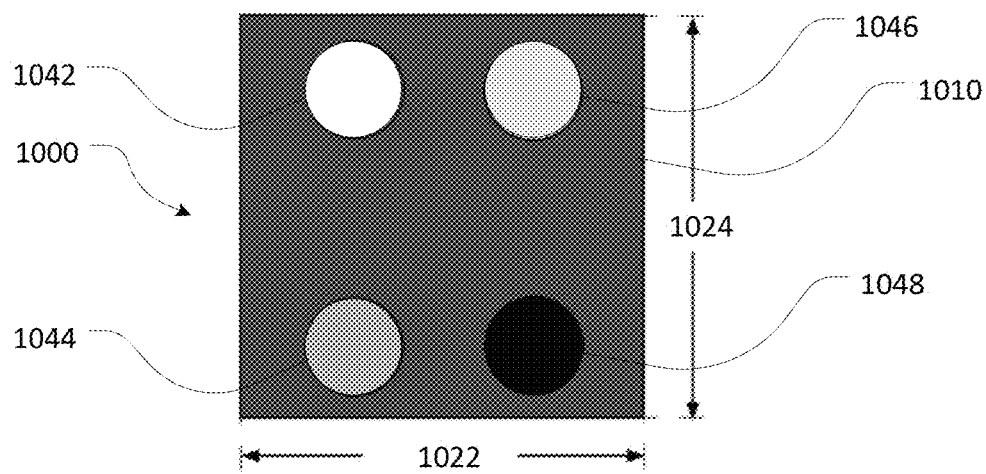
FIGS. 10A through 10C illustrate an imager camera module according to an embodiment.
Figure 10B:
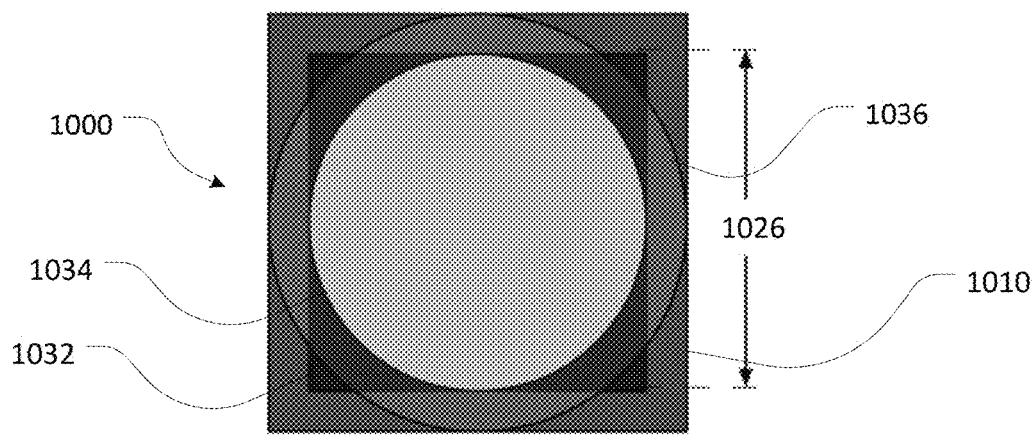
Figure 10C:
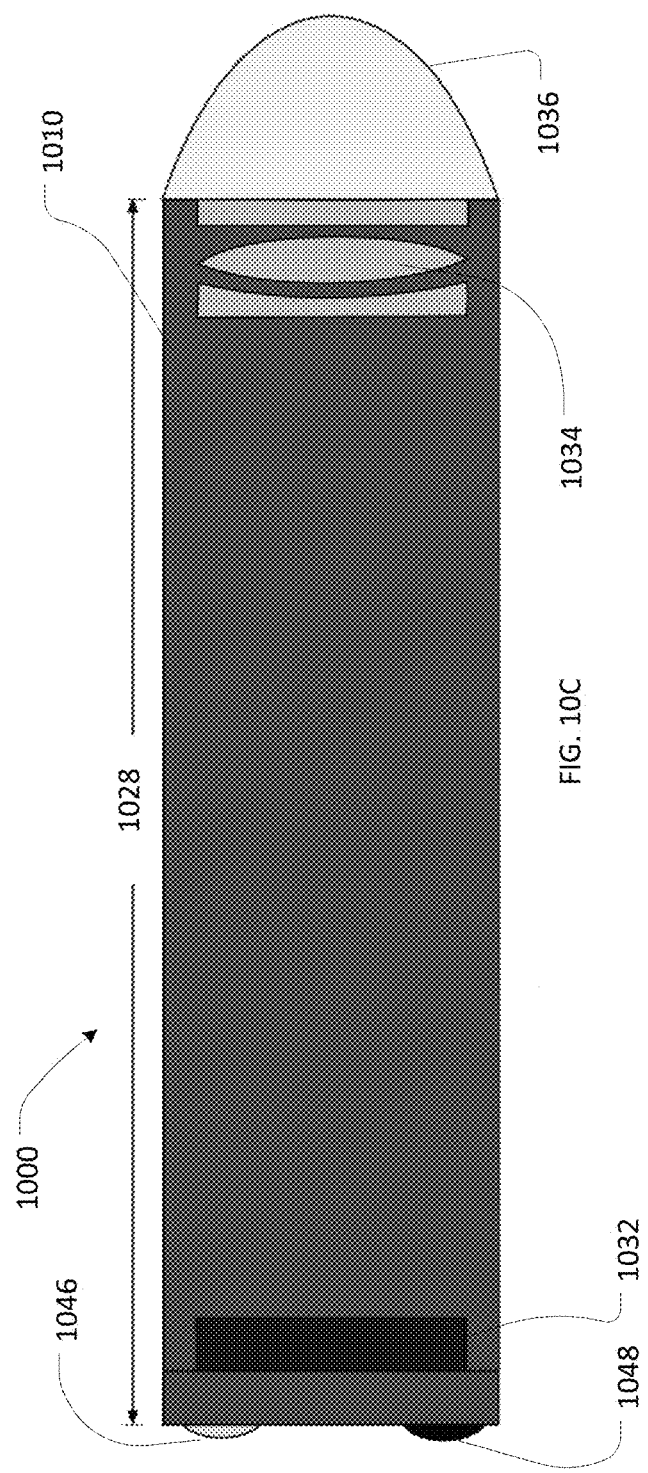

FIGS. 10A through 10C illustrate an imager camera module 1000 according to an embodiment. The imager camera module 1000 is coupled to an interposer, for example.

The imager camera module includes a substrate 1010, a plurality of contacts 1042 through 1048, an imager 1032, a lens 1034, and a cap 1036.

The plurality of contacts 1042 through 1048 include a Vdd contact 1042, a Vout contact 1044, a clock contact 1046, and a ground contact 1048. According to various embodiments, the plurality of contacts 1042 through 1048 are electrically connected to one or more cables.

The imager 1032 is powered by a voltage between the Vdd contact 1042 and the ground contact 1048, and outputs an imaging signal at the Vout contact 1044.

The lens 1034 focuses light onto the imager 1032. Although not illustrated, the lens 1034 can be a Fresnel lens.

The cap 1036 shields the internal circuitry of the imager camera module 1000 from the external environment. For example, when the imager camera module 1000 is part of a probe of an imaging needle apparatus, the cap 1036 prevents fluid from contacting the imager 1032. The cap 1036 is transparent, such that light can pass through the cap 1036, through the lens 1034, and onto the imager 1032.

Figure 11A:
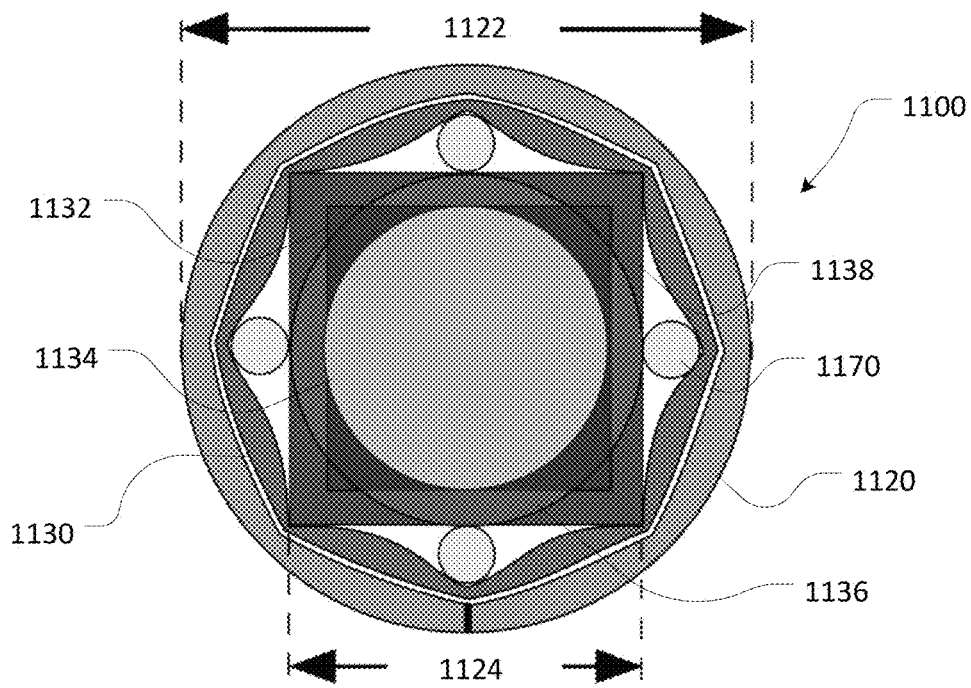
FIGS. 11A and 11B illustrate an imaging needle apparatus according to an embodiment.
Figure 11B:
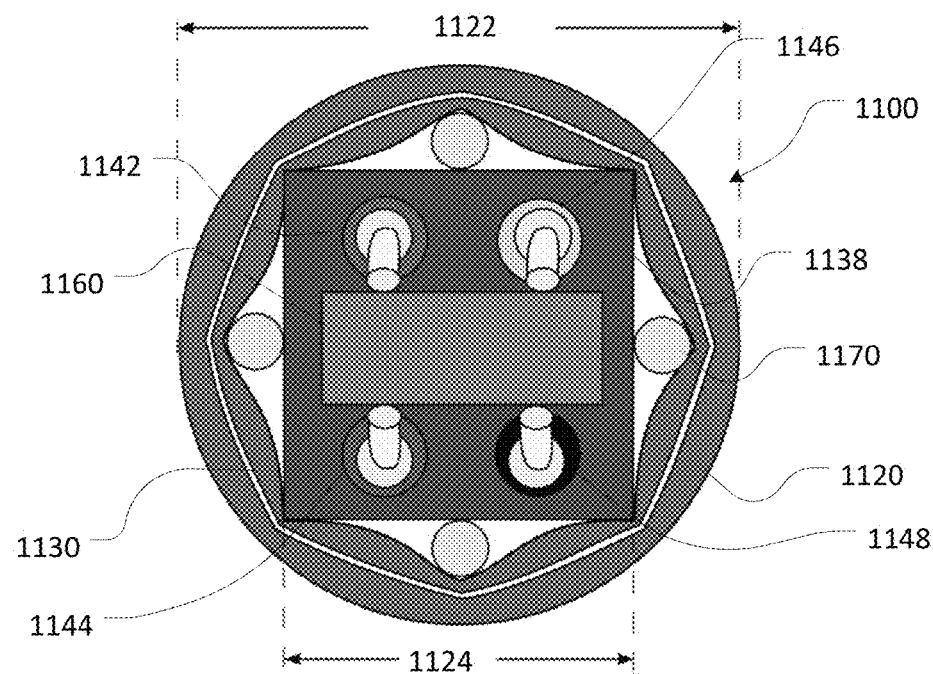

FIGS. 11A and 11B illustrate an imaging needle apparatus 1100 according to an embodiment. FIG. 11A illustrates a cross-section of the imaging needle apparatus 1100 adjacent to a distal end of the imaging needle apparatus 1100, and FIG. 11B illustrates a cross-section of the imaging needle apparatus 1100 adjacent to a proximal position of the imaging needle apparatus 1100. The proximal position is adjacent to a hub of the imaging needle apparatus 1100, for example.

The imaging needle apparatus 1100 includes a needle 1120, a probe 1130, and an interposer 1160. An outer diameter 1122 of the needle 1120 is the outer diameter of the imaging needle apparatus 1100.

The probe 1130 is disposed inside of the needle 1120 according to various embodiments. An imager module 1138 is disposed inside of the probe 1130. The imager module 1138 includes, for example, a plurality of electrical contacts 1142 through 1148, an imager 1132, a lens 1134, and a cap 1136. In a specific embodiment, the imager module 1138 is the imager camera module 1000 illustrated in FIGS. 10A through 10C. The imager module 1138 has a width 1124 that fits inside an internal surface of an outer shell of the probe 1130.

A plurality of light pipes 1170 are also disposed inside of the probe 1130.

According to various embodiments, fluid flows inside of the probe 1130. Specifically, the fluid flows in a space between the plurality of light pipes 1170 and the imager module 1138.

The interposer 1160 is coupled to the imager module 1138. The interposer is coupled between the imager module 1138 and external sources used to transmit power to the imager module 1138 and to receive imaging signals from the imager module. The interposer 1160 is disposed on a proximal end of the imager module 1138. Accordingly, the interposer 1160 connects leads into the plurality of electrical contacts 1142 through 1148, according to various embodiments.

Figure 12A:
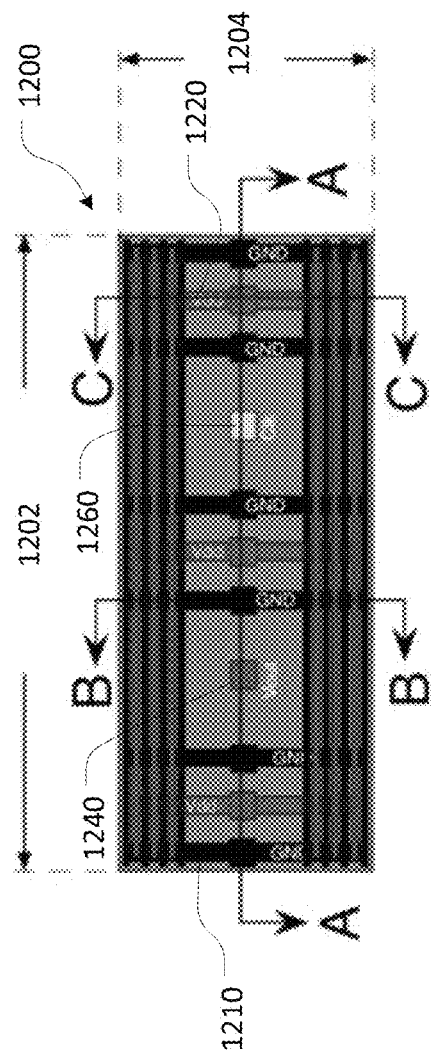
Figure 12B:
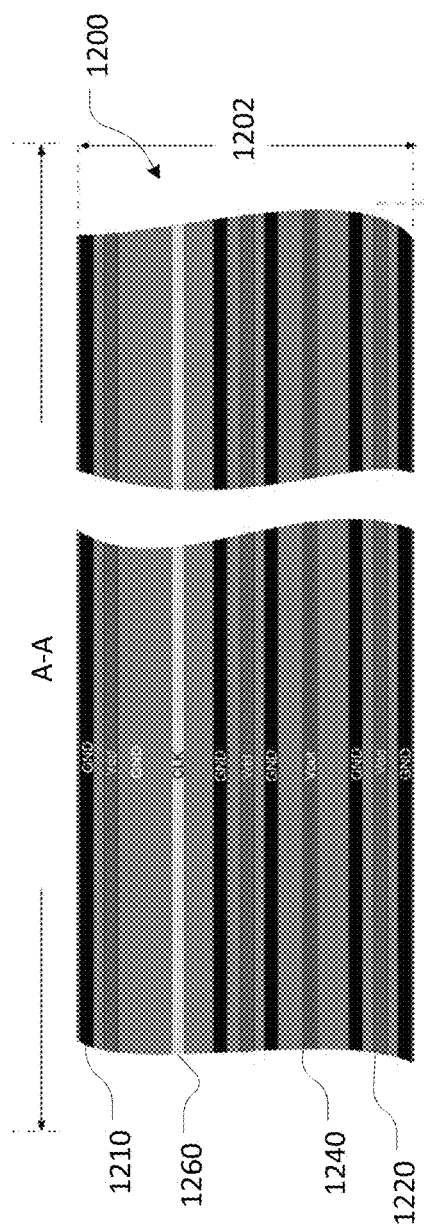

FIGS. 12A through 12D illustrate an interposer 1200 according to an embodiment. FIG. 12A illustrates the interposer 1200 from a plan view; FIG. 12B illustrates the interposer 1200 along a cross-section A-A; FIG. 12C illustrates the interposer 1200 along a cross-section B-B; and FIG. 12D illustrates the interposer 1200 along a cross-section C-C.

The interposer 1200 includes a substrate 1210, a Vdd line 1220, a ground line 1230, a Vout line 1240, and a clock line 1260. The interposer 1200 further has a width 1202 and a height 1204. The substrate 1210 is silicon, and the Vdd line 1220, the ground line 1230, the Vout line 1240, and the clock line 1260 are conductive materials according to an embodiment. The conductive materials may be doped polysilicon, tungsten, aluminum, copper, or the like.

According to various embodiments, the Vout line 1240 and the clock line 1260 carry higher-frequency signals than the Vdd line 1220 and the ground line 1230. The Vout line 1240 and the clock line 1260 illustrated in FIGS. 12A to 12D are shielded lines. Each of the Vout line 1240 and the clock line 1260 extends in a first direction. The ground line 1230 neighbors each of the Vout line 1240 and the clock line 1260 in second and third directions that are perpendicular to the first direction. An insulative material, e.g., a substrate material, is disposed between the ground line 1230 and each of the Vout line 1240 and the clock line 1260.

The ground line 1230 includes a cross-hatch pattern including a plurality of interconnects connected in a grid. That is, the ground line 1230 has a grid shape extending in the first and second directions. Similarly, the Vdd line 1220 includes a cross-hatch pattern.

As illustrated, each of the Vdd line 1220 and the ground line 1230 each extend in three dimensions. FIG. 12C shows that the ground line 1230 has the cross-hatch structure, and FIG. 12D shows that the Vdd line 1220 has a cross-hatch structure.

In contrast, the Vout line 1240 and the clock line 1260 each extend in a single direction.

According to an embodiment, the interposer 1200 is produced using photolithography, such that the Vdd line 1220, the ground line 1230, the Vout line 1240, and the clock line 1260 are three-dimensionally integrated into the substrate 1210. For example, the interposer 120 is a unitary structure having one or more electrically conductive lines that extends substantially along the length of the interposer and are insulated from each other by an insulation material (e.g., undoped semiconductor material). In an embodiment, the interposer 1200 takes up less space than an equivalent structure comprising individual wires or cables.

Figures 13A, 13B:
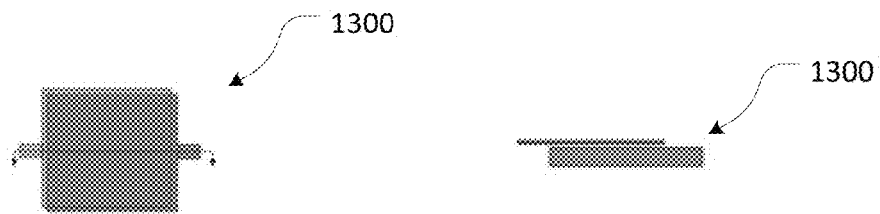
FIGS. 13A through 13C illustrate a capacitor in an interposer according to various embodiments.
Figure 13C:
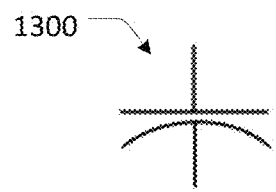

FIGS. 13A through 13C illustrate a capacitor 1300 in an interposer, according to various embodiments. FIG. 13A illustrates the capacitor 1300 from a first perspective, FIG. 13B illustrates the capacitor 1300 from a second perspective, and FIG. 13C illustrates a symbol representing the capacitor 1300.

Figures 14A, 14B:
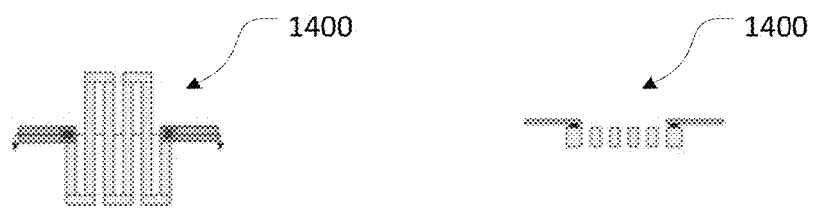
FIGS. 14A through 14C illustrate a resistor in an interposer according to various embodiments.
Figure 14C:
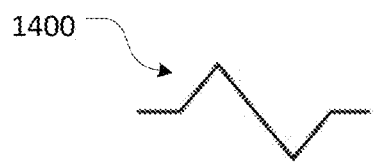

FIGS. 14A through 14C illustrate a resistor 1400 in an interposer, according to various embodiments. FIG. 14A illustrates the resistor 1400 from a first perspective, FIG. 14B illustrates the resistor 1400 from a second perspective, and FIG. 14C illustrates a symbol representing the resistor 1400.

Figure 15A:
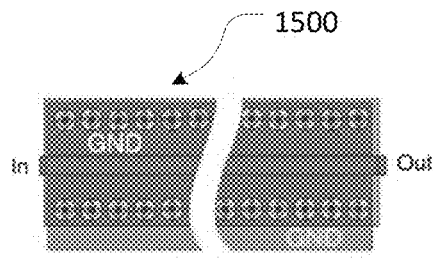
FIGS. 15A through 15E illustrate a shielded line (or cable) according to various embodiments.
Figure 15B:
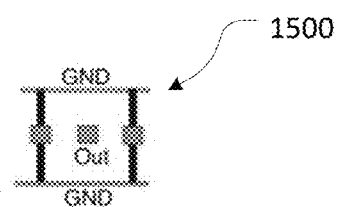
Figure 15C:
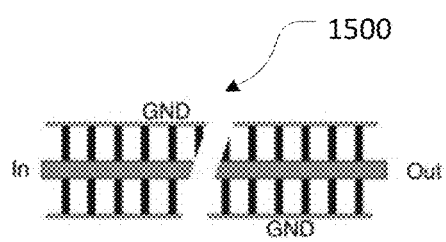
Figure 15D:
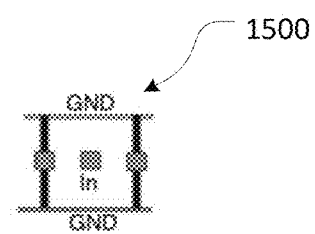
Figure 15E:
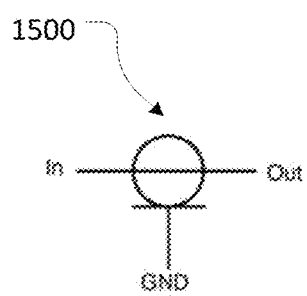

FIGS. 15A through 15C illustrate a shielded line (or cable) 1500 according to various embodiments. FIG. 15A illustrates the shielded line 1500 disposed in a substrate from a top view, FIG. 15B illustrates a line drawing of the shielded line 1500 from a front view, FIG. 15C illustrates a line drawing of the shielded line 1500 from a side view, FIG. 15D illustrates a line drawing of the shielded line 1500 from a back view, and FIG. 15E illustrates a symbol representing the shielded line 1500.

Figure 16:
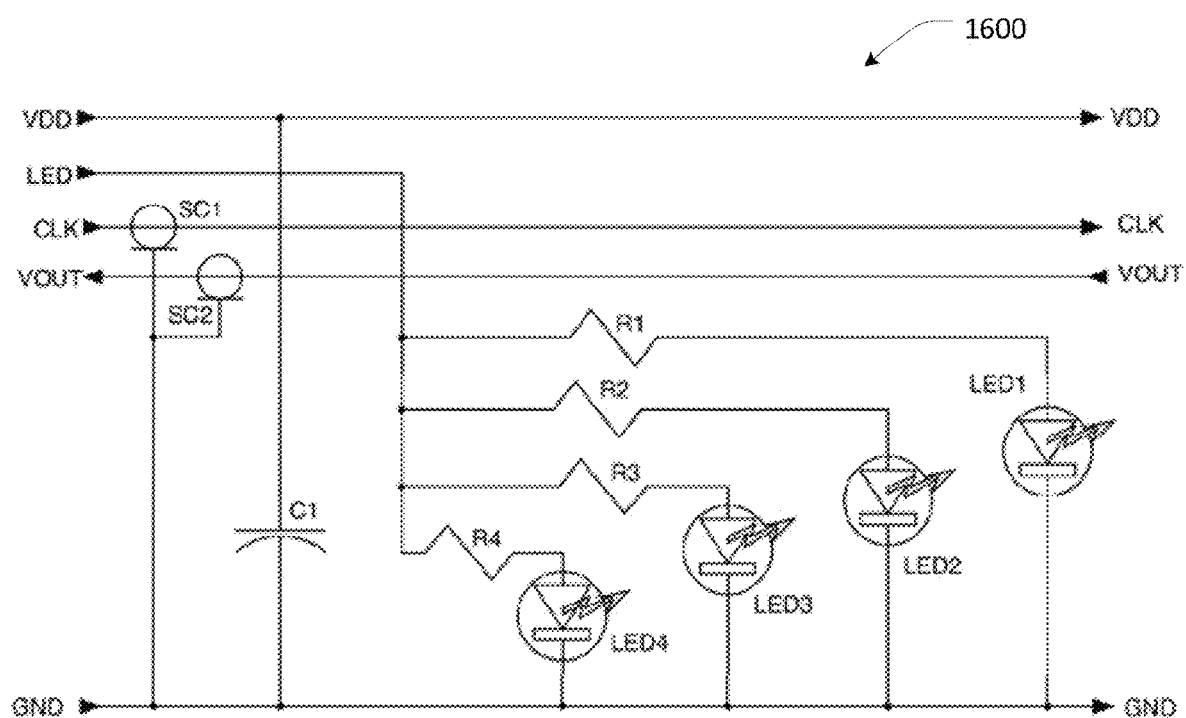
FIG. 16 illustrates a circuit diagram of an interposer according to an embodiment.

FIG. 16 illustrates a circuit diagram of an interposer 1600 according to an embodiment.

The interposer 1600 includes an imager voltage line VDD, an LED voltage line LED, a clock line CLK, and a ground line GND as inputs. The interposer 1600 further includes an imager output line VOUT as an output.

The imager voltage line VDD supplies voltage to an imager (not pictured). A capacitor C1 is connected between the imager voltage line VDD and the ground line GND.

The LED voltage line LED supplies voltage to a plurality of LEDs LED1 through LED4. The plurality of LEDs LED1 through LED4 are each connected in series to a respective resistor R1 through R4. The plurality of LEDs LED1 through LED4 are connected in parallel to each other.

The clock line CLK is connected to a first shielded line SC1. In an embodiment, the clock line CLK is further connected to an imager (not pictured).

The imager output line VOUT receives imaging signals from an imager (not pictured). The imager output line VOUT is connected to a second shielded line SC2.

The shielded lines SC1 and SC2 prevent distortion of high frequency signals running through the clock line CLK and the imager output line VOUT, for example.

Figure 17A:
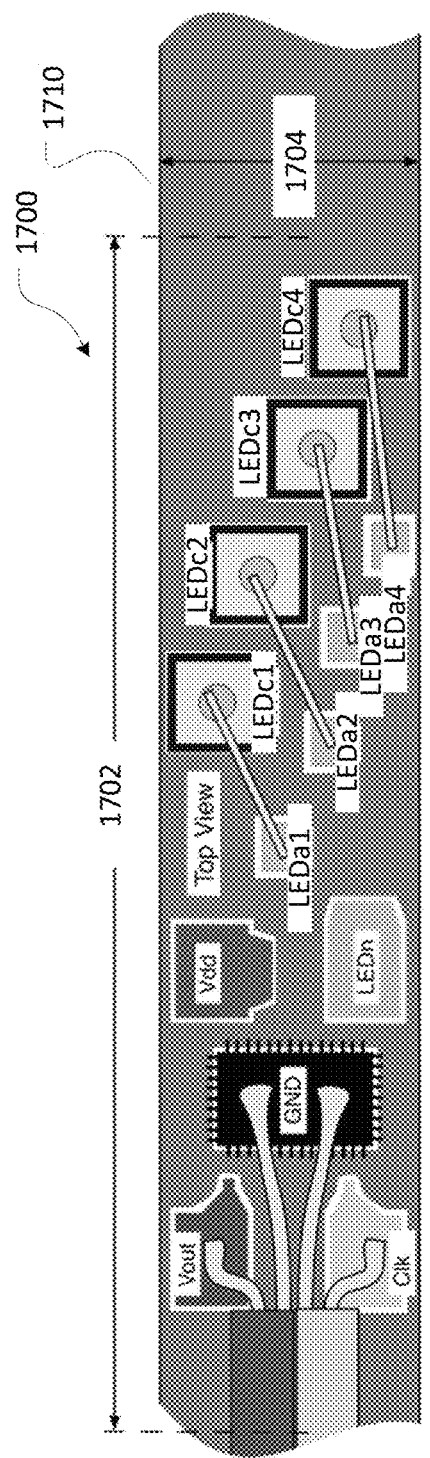
FIGS. 17A through 17C illustrate an interposer according to an embodiment.
Figure 17B:
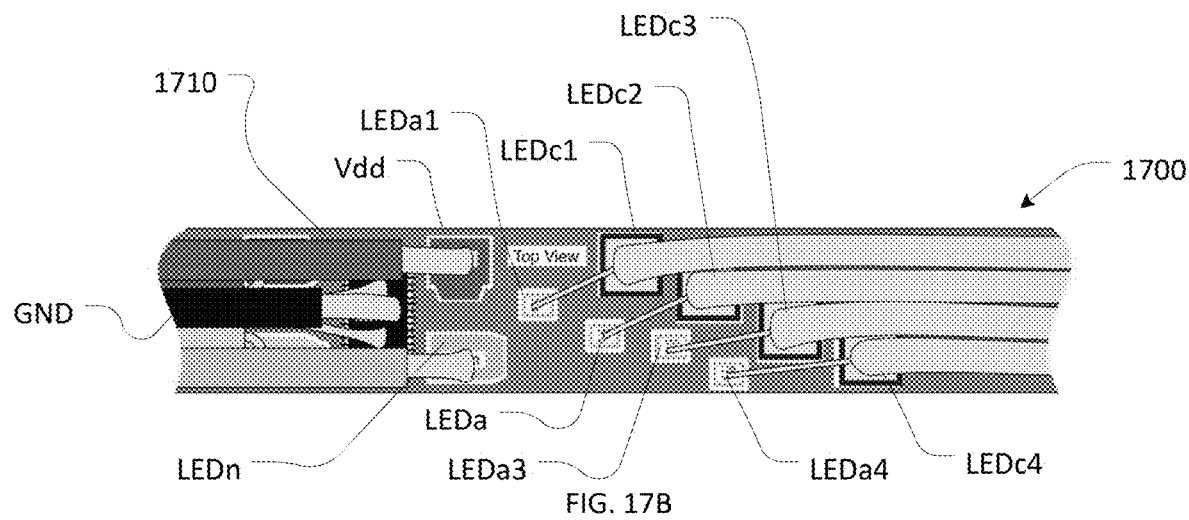
Figure 17C:
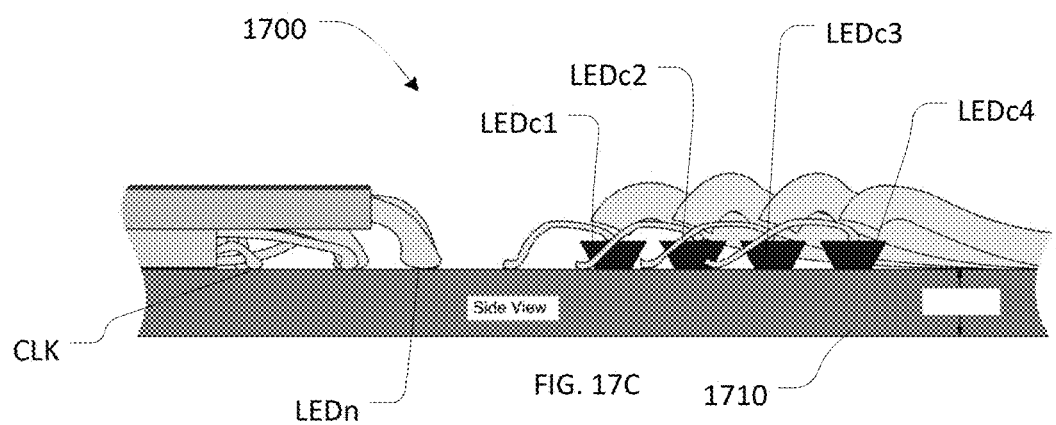

FIGS. 17A through 17C illustrate an interposer 1700 according to an embodiment. FIG. 17A is a plan view of the interposer 1700 without attached input and output structures. FIG. 17B is a plan view of the interposer 1700 with attached input and output structures. FIG. 17C is a side view of the interposer 1700 with attached input and output structures.

The interposer 1700 includes a substrate 1710 and a plurality of contacts disposed in the substrate. The contacts include an output voltage contact Vout, a clock contact Clk, a ground contact GND, an imager voltage contact Vdd, an LED voltage contact LEDn, and first through fourth LED contacts LEDa1 through LEDa4. In addition, first through fourth LEDs LEDc1 through LEDc4 are coupled to the substrate 1710, and electrically connected to the LED contacts LEDa1 through LEDa4.

According to various embodiments, the output voltage contact Vout receives imaging signals from an imager, the clock contact Clk is electrically connected to the imager, the ground contact GND is electrically connected to the imager and the first through fourth LEDs LEDc1 through LEDc4, the imager voltage contact Vdd is electrically connected to the imager, the and the LED voltage contact LEDn is electrically connected to each of the first through fourth LED contacts LEDa1 through LEDa4.

As illustrated in FIG. 17A, an area occupied by the contacts and LEDs coupled to the interposer substrate 1710 has a width 1702 and a height 1704. The output voltage contact Vout, the clock contact Clk, the ground contact GND, the imager voltage contact Vdd, and the LED voltage contact LEDn are located in two-dimensionally staggered positions along a surface of the substrate 1710. In addition, the first through fourth LEDs LEDc1 through LEDc4 are located in two-dimensionally staggered positions along the surface of the substrate 1710.

FIGS. 17B and 17C show the interposer 1700 attached to various other input and output structures according to an embodiment. For example, the output voltage contact Vout is connected to an output voltage cable or wire, clock contact Clk is connected to a clock cable, the ground contact GND is connected to a ground cable, the imager voltage contact Vdd is connected to an imager voltage cable, and the LED voltage contact LEDn is connected to an LED voltage cable. The cables are soldered to the contacts, for example. In addition, the fist through fourth LEDs LEDc1 through LEDc4 are optically coupled to first through fourth light pipes LEDp1 through LEDp4.

Because the output voltage contact Vout, the clock contact Clk, the ground contact GND, the imager voltage contact Vdd, and the LED voltage contact LEDn are located in two-dimensionally staggered positions along a surface of the substrate 1710, the cables attached to the contacts extend parallel to each other along the surface of the substrate 1710. Similarly, since the first through fourth LEDs LEDc1 through LEDc4 are located in two-dimensionally staggered positions along the surface of the substrate 1710, the light pipes extend parallel to each other along the surface of the substrate 1710.

According to various embodiments, the interposer includes several components that are described in the following Table 1. However, other components may be used in alternative embodiments.

| Component Type | Specifications | Vendor/Construction |
| --- | --- | --- |
| Bypass Capacitor | 0.1 uf Low ESR & L | Metal to Metal Capacitor Built into the Interposer |
| Resistor | 100 Ohms | Interposer poly silicon resistor at 2 Ohms per square for 50 squares |

-continued

| Component Type | Specifications | Vendor/Construction |
|---|---|---|
| Shielded Cable | Approximately 50 Ohms of Characteristic Impedance. | Constructed within the interposer with metal layers and dielectric layers |
| Gen 3 CREE LED Die CxxxUT190-Sxxxx-31 | High efficiency, Ultra Thin LED 190 um × 190 um by 50 um Thickness | CREE, Gen3, InGaN material blue LEDs. Low forward voltage, 2.9 V @ 5 mA. |

Figure 18C:
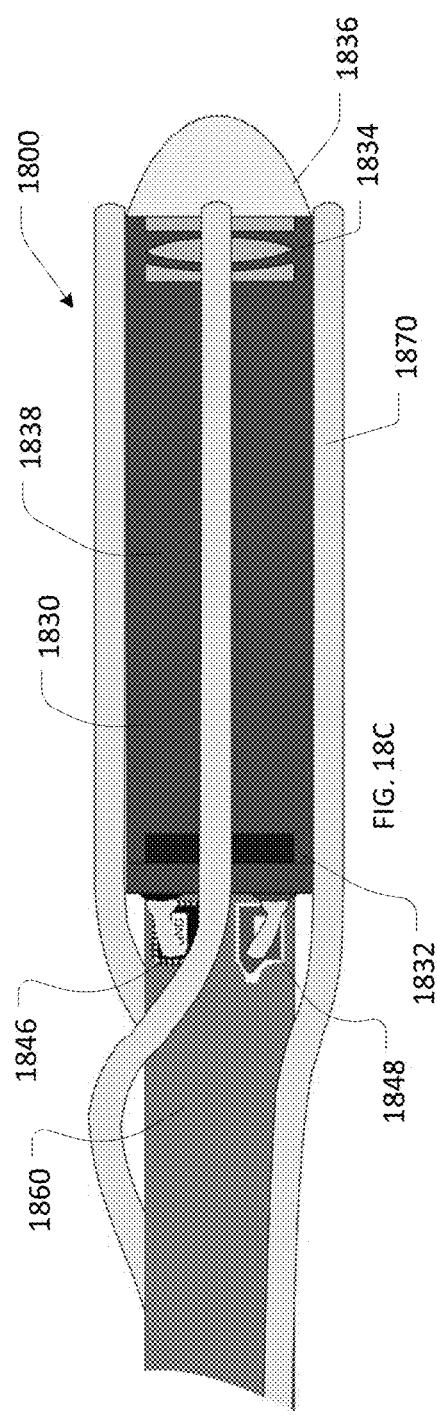
Figure 18D:
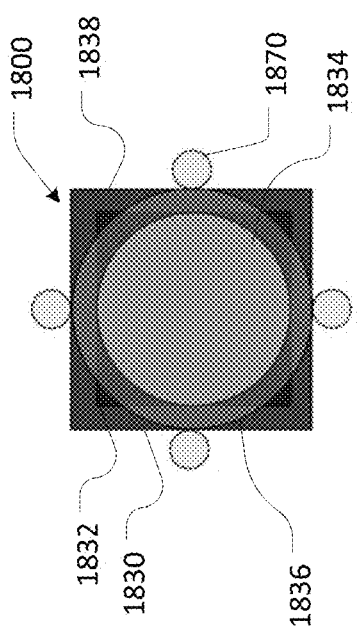

FIGS. 18A through 18D illustrate an imaging apparatus 1800 according to an embodiment. FIGS. 18A through 18C each show a cross-sectional view of the imaging apparatus 1800. FIG. 18D shows a front view of the imaging apparatus 1800. The apparatus 1800 includes an imaging module 1830 coupled to an interposer structure 1860, and a plurality of light pipes 1870.

The imaging module 1830 includes an imager 1832, a lens 1834, and a cover 1836. The interposer 1860 includes a plurality of contacts that are electrically coupled to the imaging module 1830. The light pipes 1870 are disposed on a side of the interposer, and then wrap evenly around the outer surface of the imaging module 1830. For example, the imaging module 1830 has a square cross-section perpendicular to an axis direction of the apparatus 1800, and the light pipes 1870 are each disposed on each of the four sides of the imaging module 1830.

FIGS. 19A through 19E illustrate an end of an imaging apparatus 1900 according to various embodiments. The apparatus 1900 includes a needle 1920 and a probe 1930, which may be retracted or extended from an end of the needle 1920.

Figure 19A:
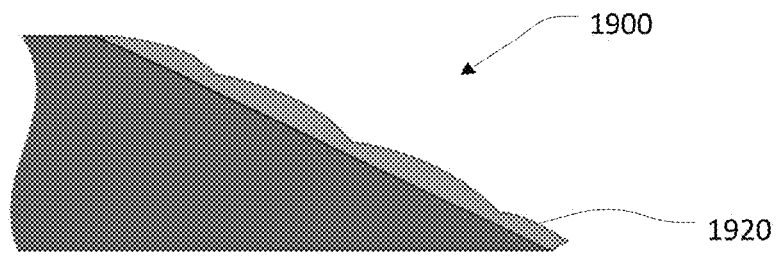
FIGS. 19A through 19E illustrate an end of an imaging apparatus according to various embodiments.

FIG. 19A illustrates a side of the apparatus 1900 when the probe 1930 is fully retracted from a tip of the needle 1920.

Figure 19B:
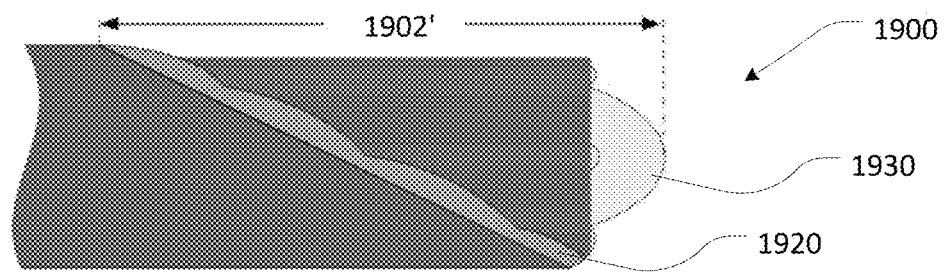

FIG. 19B illustrates a side of the apparatus 1900 when the probe 1930 is partially extended from the tip of the needle 1920. An end of the probe 1930 is disposed a first distance 1902' from a proximal edge of the needle 1920.

Figure 19C:
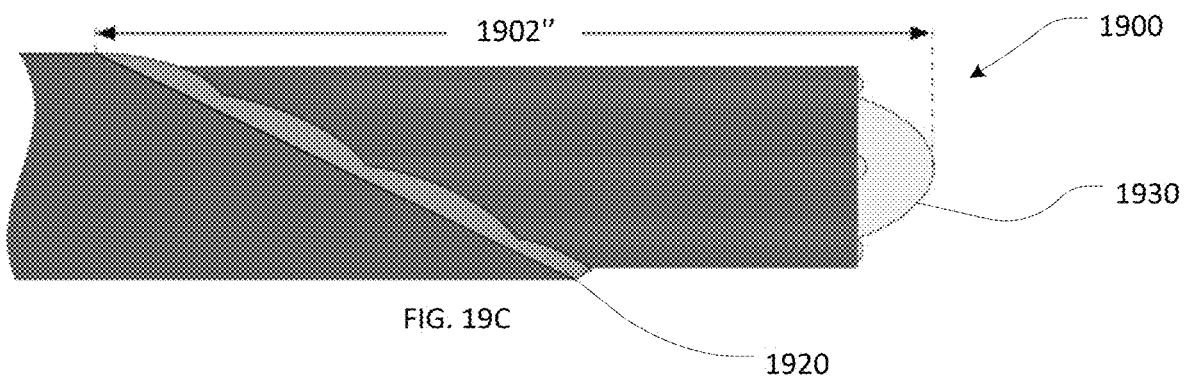

FIG. 19C illustrates a side of the apparatus 1900 when the probe 1930 is partially extended from the tip of the needle 1920. The end of the probe 1930 is disposed a second distance 1902" from the proximal edge of the needle 1920. The second distance 1902" is longer than the first distance 1902'.

Figure 19D:
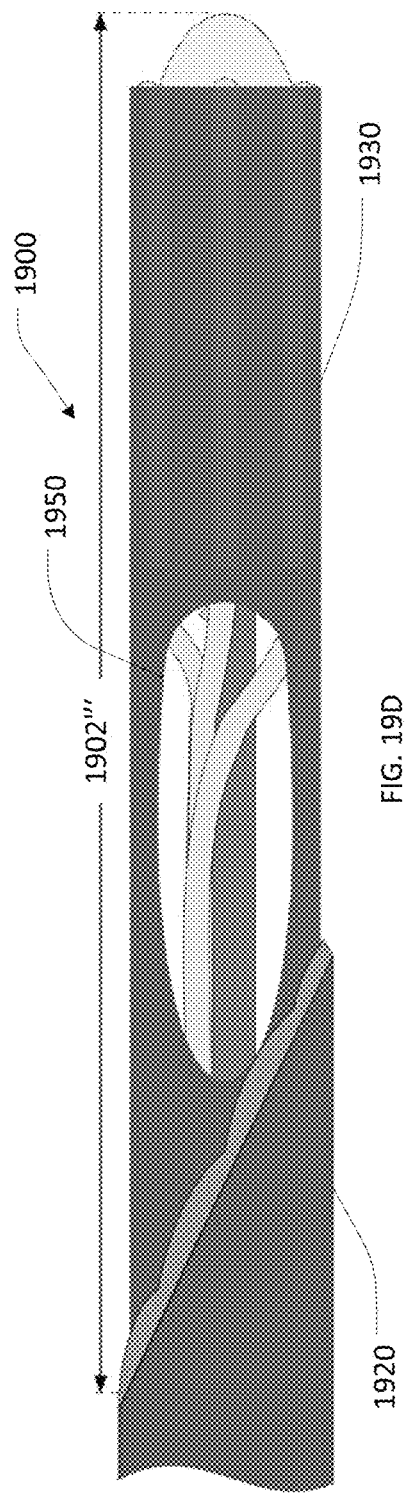

FIG. 19D illustrates a side of the apparatus 1900 when the probe 1930 is extended from the tip of the needle 1920. In the embodiment illustrated in FIG. 19D, a side port 1950 of the probe 1930 is exposed. The end of the probe 1930 is disposed a third distance 1902'" from the proximal edge of the needle 1920. The third distance 1902'" is longer than the second distance 1902"'.

Figure 19E:
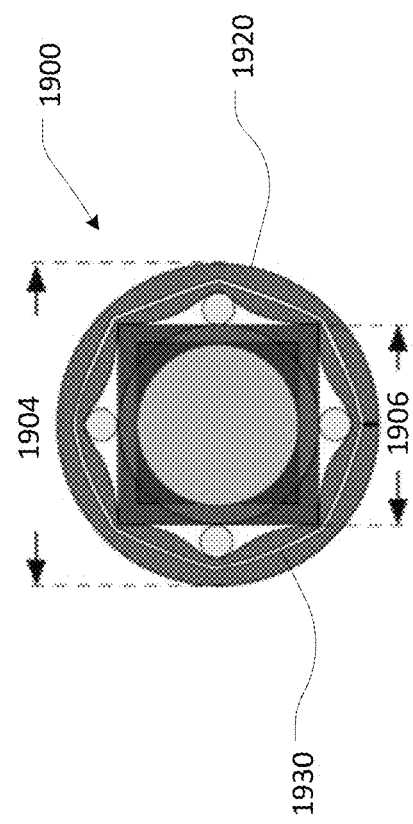

FIG. 19E illustrates a front of the apparatus 1900. The needle 1920 has an outer diameter 1904, and the probe 1930 has a width 1906 that is shorter than the outer diameter 1904.

According to various embodiments of the present disclosure, an imaging needle apparatus can have relatively small dimensions. For example, a needle in the imaging needle apparatus may be a 19.5 gauge needle that has a length of up to 100 mm. When a probe is fully extended, it may extend up to 6.4 mm in front of a tip of the needle.

An outer diameter of the needle may be less than 1 mm, e.g., 994 um and an inner diameter of a lumen in the probe may be 744 um at a cross section that is 10 mm from a hub of the imaging needle apparatus, and 6 mm from the tip of the needle. An imager module disposed inside of the probe may have a height and a width of 630 um. An imager in the imaging module may have a height and a width of 500 um. The imager module may have a length of 2270 um.

The outer diameter of the needle may be significantly smaller than standard arthroscopic needles, which may have diameters of 2.11 mm to 4.57 mm.

An interposer in the imaging needle apparatus may have a width of 500 um, a thickness of 200 um, and a length of up to 100 mm. Lines in the interposer may be spaced apart by 1 um. Each of the lines in the interposer may have a width of 5 um.

Contacts of the interposer may occupy an area with a width of 2.3 mm and a height of 500 um. A substrate of the interposer may have a thickness of 200 um.

Figure 20:
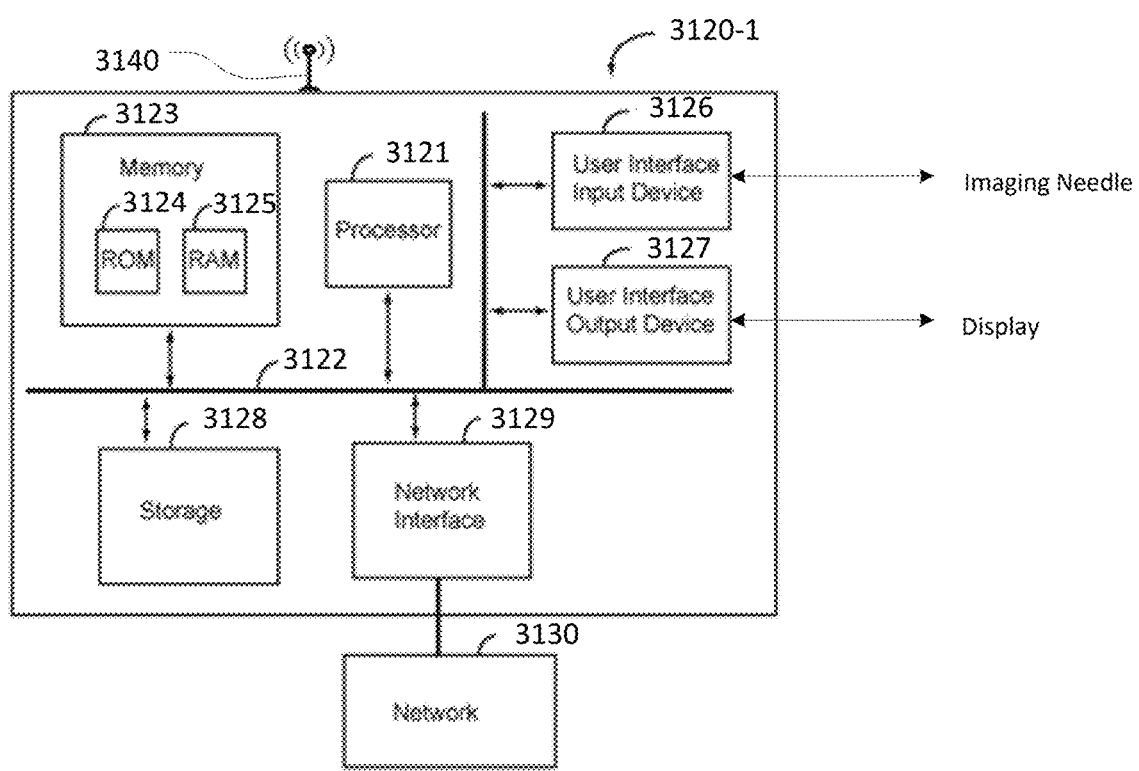
FIG. 20 illustrates a computer system according to an embodiment of the disclosure.

According to various embodiments, the imaging needle has the following specifications:
Needle Gauge: 19.5 Gauge
Puncture Diameter: 0.994 mm
Puncture Area: 0.78 mm$^2$
Equivalent Distal Tip Lumen size: 0.06 mm$^2$
Equivalent Side Lumen size: 0.32 mm$^2$
Pixel Size: 2.5 um by 2.5 um
Pixel Count: 40,000 pixels
Imager Active Area: 0.25 mm$^2$
Lens Diameter: 500 um
First focal length: 200 um at 1× zoom and 60 degree field of view (FOV)
Second focal length: 400 um at 2× zoom and 30 degree FOV
Third focal length: 800 um at 4× zoom and 15 degree FOV FIG. 20 illustrates a computer system according to an embodiment of the disclosure.

A computer system 3120-1 may include one or more of a processor 3121, a memory 3123, a user input device 3126, a user output device 3127, and a storage 3128, each of which communicates through a bus 3122. The computer system 3120-1 may also include a network interface 3129 that is coupled to a network 3130. The processor 3121 may be a central processing unit (CPU) or a semiconductor device that executes processing instructions stored in the memory 3123 and/or the storage 3128. The memory 3123 and the storage 3128 may include various forms of volatile or non-volatile storage media. For example, the memory may include a read-only memory (ROM) 3124 and a random access memory (RAM) 3125.

Accordingly, an embodiment of the invention may be implemented as a computer implemented method or as a non-transitory computer readable medium with computer executable instructions stored thereon. In an embodiment, when executed by the processor, the computer readable instructions may perform a method according to at least one aspect of the invention.

In an embodiment, the user interface output device 3127 may be coupled to a display. The display may be configured to display images and/or videos output through the bus 3122.

The user interface input device 3126 may be coupled to an imaging needle apparatus, via a wired or wireless connection. The user interface input device 3126 may receive image signals from the imaging needle apparatus, corresponding to images captured by an imager assembly of the imaging needle apparatus. The processor 3121 may convert the image signals into a format suitable for output to the display. For example, the processor 3121 may filter the image signals. In an embodiment, the processor 3121 may be integrated into an IC stack within a probe of the imaging needle apparatus.

The computer system 3120-1 may further include a wireless transceiver 3140. The wireless transceiver 3140 may transmit signals from the bus 3122 to an external device, and/or receive signals from an external device. For example, the wireless transceiver 3140 may transmit imaging signals to the display, and/or may receive imaging signals from the imaging needle apparatus.

According to various embodiments, the computer system 3120-1 supplies voltage to the imaging needle apparatus, and processes the imaging signals received from the imaging needle apparatus. That is, the computer system 3120-1 is an embodiment of an external device coupled to the imaging needle apparatus.

Figure 21:
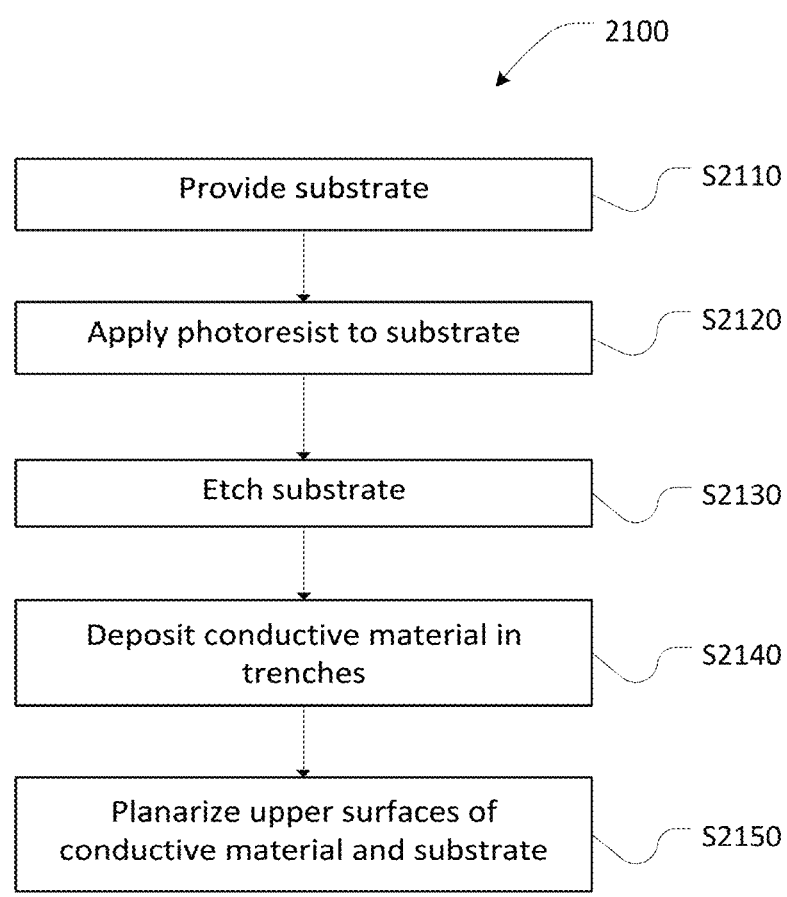
FIG. 21 illustrates a process of forming an interposer according to an embodiment.

FIG. 21 illustrates a process 2100 of forming an interposer according to an embodiment.

At S2110, a substrate is provided. According to an embodiment, the substrate includes a semiconductor material. For example, the substrate includes polysilicon.

At S2120, photoresist is applied to the substrate. In a specific embodiment, the photoresist is applied by spin-coating the photoresist onto a surface of the substrate. According to various embodiments, the photoresist is a positive photoresist (e.g., DNQ-Novolac photoresist) or a negative photoresist (e.g., SU-8 photoresist). The photoresist is patterned using a photomask.

The substrate is etched at S2140 using the patterned photoresist. In an embodiment, exposed portions of the substrate are etched using a dry etch process.

At S2150, a conductive material is deposited in the trenches to be used as conductive lines such as a Vdd line 1220, a ground line 1230, a Vout line 1240, and a clock line 1260.

At S2160, in an embodiment, an upper surface of the conductive material and the substrate are planarized. The substrate is cut or diced into a plurality of pieces to obtain interposers for use in an image apparatus, such as the image apparatus illustrated in FIGS. 1A and 1B.

From the foregoing, it will be appreciated that various embodiments of the present disclosure have been described herein for purposes of illustration, and that various modifications may be made without departing from the scope and spirit of the present disclosure. For example, the present invention may be applied to imaging devices other than imaging needle apparatus, e.g., an imaging device having a stent without a needle or the like. Accordingly, the various embodiments disclosed herein are not intended to be limiting.

What is claimed is:

1. An imaging apparatus, comprising:
 a hub;
 a needle extending from the hub;
 a probe provided within the needle and configured to extend and retract;
 an imager disposed in the probe, the imager being configured to generate an imaging signal;
 an interposer provided within the needle and including a substrate and a conductive line patterned on the substrate, the interposer being configured to receive the image signal from the imager via the conductive line; and
 a lumen configured to hold fluid, the lumen extending through the hub and the probe,
 wherein the interposer is disposed inside of the lumen, and
 wherein the probe has one or more side ports coupled to the lumen, the one or more side ports being covered by the needle when the probe is in a first position, the one or more side ports being exposed when the probe is in a second position.

2. The apparatus of claim 1, wherein the imager includes a plurality of photocells configured to generate the imaging signal.

3. The apparatus of claim 2, wherein the interposer includes first through third contacts, the first contact receiving the imaging signal from the imager, the second contact outputting an imager voltage to the imager, the third contact outputting a ground voltage to the imager,
 wherein a shielded line is coupled between the first contact and the imager.

4. The apparatus of claim 3, wherein the shielded line includes a central line, a ground line, and an insulator disposed between the central line and the ground line, the ground line having a cross-hatched structure.

5. The apparatus of claim 2, wherein the probe further comprises:
 a cover, the cover being transparent; and
 a lens disposed between the imager and the cover, the lens being configured to focus light on the plurality of photocells.

6. The apparatus of claim 1, wherein the interposer is covered in a hydrophobic sealant.

7. The apparatus of claim 1, further comprising:
 a fitting coupled to the hub, the hub being coupled between the fitting and the needle, the fitting being configured to form a fluid-tight seal with a pressure source,
 wherein the lumen extends through the fitting.

8. The apparatus of claim 1, further comprising:
 a plurality of light pipes disposed between the probe and the needle; and
 a plurality of light sources optically coupled to the plurality of light pipes.

9. The apparatus of claim 8, wherein the interposer includes a fourth contact and a fifth contact, the fourth contact outputting a voltage to the plurality of light sources, the fifth contact outputting a ground voltage to the plurality of light sources.

* * * * *